(12) United States Patent
Kirkham et al.

(10) Patent No.: US 7,820,789 B2
(45) Date of Patent: Oct. 26, 2010

(54) MUTANT PNEUMOLYSIN PROTEINS

(76) Inventors: Lea-Ann Stirling Kirkham, 42 Robertson Road, Kardinya, Perth (AU) 6163; Timothy John Mitchell, Station House, Station Road, Rhu, Hellensburgh (GB) G84 8LW ( * ) Notice: Subject to any disclaimer, the term of this patent is extended or adjusted under 35 U.S.C. 154(b) by 146 days.

(21) Appl. No.: 11/568,802

(22) PCT Filed: May 9, 2005

(86) PCT No.: PCT/GB2005/001792
§ 371 (c)(1), (2), (4) Date: Aug. 16, 2007

(87) PCT Pub. No.: WO2005/108580
PCT Pub. Date: Nov. 17, 2005

(65) Prior Publication Data
US 2008/0112964 A1    May 15, 2008

Related U.S. Application Data

(60) Provisional application No. 60/569,415, filed on May 7, 2004.

(30) Foreign Application Priority Data
May 7, 2004  (GB) .................................. 0410220.8

(51) Int. Cl.
*C07K 14/00* (2006.01)

(52) U.S. Cl. ........................ 530/350; 530/300; 435/7.1; 435/325

(58) Field of Classification Search ....................... None
See application file for complete search history.

(56) References Cited

U.S. PATENT DOCUMENTS 5,565,204 A    10/1996    Kuo et al.

OTHER PUBLICATIONS

Wells, Biochemistry, vol. 29, pp. 8509-8517, 1990.*
Seffernick et al. (J. Bacteriology, vol. 183, pp. 2405-2410, 2001.*

* cited by examiner

*Primary Examiner*—Hope A Robinson
(74) *Attorney, Agent, or Firm*—Dann, Dorfman, Herrell & Skillman; Kathleen D. Rigaut

(57) ABSTRACT

The invention relates to immunogenic compositions comprising mutant *Streptococcus pneumoniae* pneumolysin proteins. The invention further relates to such proteins and nucleic acids encoding these proteins. In particular embodiments, the invention is directed to an isolated mutant pneumolysin (PLY) protein, wherein the mutant PLY protein differs from the wild-type PLY protein of SEQ ID NO:1 presence of a mutation within the region of amino acids 144 to 161 of the wild type such that the toxicity of the mutant is reduced relative to that of the wild-type protein. In particular embodiments, the mutant PLY protein differs from the wild-type protein by the substitution or deletion of amino acids including the deletion of two adjacent amino acids within the region of amino acids 144 to 151 of the wild-type sequence.

27 Claims, 14 Drawing Sheets

Pneumolysin    from *Streptococcus pneumoniae*
Length: 471   AA         g.i. 47403 (X52474)

```
1    MANKAVNDFI  LAMNYDKKKL  LTHQGESIEN  RFIKEGNQLP  DEFVVIERKK
51   RSLSTNTSDI  SVTATNDSRL  YPGALLVVDE  TLLENNPTLL  AVDRAPMTYS
101  IDLPGLASSD  SFLQVEDPSN  SSVRGAVNDL  LAKWHQDYGQ  VNNVPARMQY
151  EKITAHSMEQ  LKVKFGSDFE  KTGNSLDIDF  NSVHSGEKQI  QIVNFKQIYY
201  TVSVDAVKNP  GDVFQDTVTV  EDLKQRGISA  ERPLVYISSV  AYGRQVYLKL
251  ETTSKSDEVE  AAFEALIKGV  KVAPQTEWKQ  ILDNTEVKAV  ILGGDPSSGA
301  RVVTGKVDMV  EDLIQEGSRF  TADHPGLPIS  YTTSFLRDNV  VATFQNSTDY
351  VETKVTAYRN  GDLLLDHSGA  YVAQYYITWN  ELSYDHQGKE  VLTPKAWDRN
401  GQDLTAHFTT  SIPLKGNVRN  LSVKIRECTG  LAWEWWRTVY  EKTDLPLVRK
451  RTISIWGTTL  YPQVEDKVEN  D
```

Figure 1

SEQUENCE LISTING

<160> NUMBER OF SEQ ID NOS: 21

<210> SEQ ID NO 1
<211> LENGTH: 471
<212> TYPE: PRT
<213> ORGANISM: Streptococcus pneumoniae

<400> SEQUENCE: 1

```
Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190
```

```
Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Lys
        210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
        275                 280                 285

Ala Val Ile Leu Gly Gly Asp Pro Ser Ser Gly Ala Arg Val Val Thr
        290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
            340                 345                 350

Thr Lys Val Thr Ala Tyr Arg Asn Gly Asp Leu Leu Leu Asp His Ser
        355                 360                 365

Gly Ala Tyr Val Ala Gln Tyr Tyr Ile Thr Trp Asn Glu Leu Ser Tyr
        370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
            420                 425                 430

Trp Glu Trp Trp Arg Thr Val Tyr Glu Lys Thr Asp Leu Pro Leu Val
        435                 440                 445

Arg Lys Arg Thr Ile Ser Ile Trp Gly Thr Thr Leu Tyr Pro Gln Val
        450                 455                 460

Glu Asp Lys Val Glu Asn Asp
465                 470

<210> SEQ ID NO 2
<211> LENGTH: 18
<212> TYPE: PRT
<213> ORGANISM: Streptococcus pneumoniae

<400> SEQUENCE: 2

Val Pro Ala Arg Met Gln Tyr Glu Lys Ile Thr Ala His Ser Met Glu
1               5                   10                  15

Gln Leu

<210> SEQ ID NO 3
<211> LENGTH: 8
<212> TYPE: PRT
<213> ORGANISM: Streptococcus pneumoniae

<400> SEQUENCE: 3

Val Pro Ala Arg Met Gln Tyr Glu
1               5
```

<210> SEQ ID NO 4
<211> LENGTH: 42
<212> TYPE: PRT
<213> ORGANISM: Homo sapiens

<400> SEQUENCE: 4

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 5
<211> LENGTH: 18
<212> TYPE: PRT
<213> ORGANISM: Streptococcus pneumoniae

<400> SEQUENCE: 5

Trp His Gln Asp Tyr Gly Gln Val Asn Asn Val Pro Ala Arg Met Gln
1               5                   10                  15

Tyr Glu

<210> SEQ ID NO 6
<211> LENGTH: 32
<212> TYPE: DNA
<213> ORGANISM: Artificial sequence
<220> FEATURE:
<223> OTHER INFORMATION: Primer

<400> SEQUENCE: 6
cgatttgttg gctaagcaag attatggtca gg                                    32

<210> SEQ ID NO 7
<211> LENGTH: 32
<212> TYPE: DNA
<213> ORGANISM: Artificial sequence
<220> FEATURE:
<223> OTHER INFORMATION: Primer

<400> SEQUENCE: 7
cctgaccata atcttgctta gccaacaaat cg                                    32

<210> SEQ ID NO 8
<211> LENGTH: 39
<212> TYPE: DNA
<213> ORGANISM: Artificial sequence
<220> FEATURE:
<223> OTHER INFORMATION: Primer

<400> SEQUENCE: 8
gttggctaag tggcattatg gtcaggtcaa taatgtccc                             39

<210> SEQ ID NO 9
<211> LENGTH: 39
<212> TYPE: DNA
<213> ORGANISM: Artificial sequence
<220> FEATURE:
<223> OTHER INFORMATION: Primer

<400> SEQUENCE: 9
gggacattat tgacctgacc ataatgccac ttagccaac                             39

<210> SEQ ID NO 10

```
<211> LENGTH: 36
<212> TYPE: DNA
<213> ORGANISM: Artificial sequence
<220> FEATURE:
<223> OTHER INFORMATION: Primer

<400> SEQUENCE: 10
ggctaagtgg catcaagatc aggtcaataa tgtccc                          36

<210> SEQ ID NO 11
<211> LENGTH: 36
<212> TYPE: DNA
<213> ORGANISM: Artificial sequence
<220> FEATURE:
<223> OTHER INFORMATION: Primer

<400> SEQUENCE: 11
gggacattat tgacctgatc ttgatgccac ttagcc                          36

<210> SEQ ID NO 12
<211> LENGTH: 34
<212> TYPE: DNA
<213> ORGANISM: Artificial sequence
<220> FEATURE:
<223> OTHER INFORMATION: Primer

<400> SEQUENCE: 12
ggcatcaaga ttatggtaat aatgtcccag ctag                            34

<210> SEQ ID NO 13
<211> LENGTH: 34
<212> TYPE: DNA
<213> ORGANISM: Artificial sequence
<220> FEATURE:
<223> OTHER INFORMATION: Primer

<400> SEQUENCE: 13
ctagctggga cattattacc ataatcttga tgcc                            34

<210> SEQ ID NO 14
<211> LENGTH: 31
<212> TYPE: DNA
<213> ORGANISM: Artificial sequence
<220> FEATURE:
<223> OTHER INFORMATION: Primer

<400> SEQUENCE: 14
ggtcaggtca ataatgctag aatgcagtat g                               31

<210> SEQ ID NO 15
<211> LENGTH: 31
<212> TYPE: DNA
<213> ORGANISM: Artificial sequence
<220> FEATURE:
<223> OTHER INFORMATION: Primer

<400> SEQUENCE: 15
catactgcat tctagcatta ttgacctgac c                               31

<210> SEQ ID NO 16
<211> LENGTH: 41
<212> TYPE: DNA
<213> ORGANISM: Artificial sequence
<220> FEATURE:
<223> OTHER INFORMATION: Primer

<400> SEQUENCE: 16
```

```
ggtcaataat gtcccaatgc agtatgaaaa aataacggct c                                41

<210> SEQ ID NO 17
<211> LENGTH: 41
<212> TYPE: DNA
<213> ORGANISM: Artificial sequence
<220> FEATURE:
<223> OTHER INFORMATION: Primer

<400> SEQUENCE: 17
gagccgttat tttttcatac tgcattggga cattattgac c                               41

<210> SEQ ID NO 18
<211> LENGTH: 41
<212> TYPE: DNA
<213> ORGANISM: Artificial sequence
<220> FEATURE:
<223> OTHER INFORMATION: Primer

<400> SEQUENCE: 18
ggtcaataat gtcccagcta gatatgaaaa aataacggct c                               41

<210> SEQ ID NO 19
<211> LENGTH: 41
<212> TYPE: DNA
<213> ORGANISM: Artificial sequence
<220> FEATURE:
<223> OTHER INFORMATION: Primer

<400> SEQUENCE: 19
gagccgttat tttttcatat ctagctggga cattattgac c                               41

<210> SEQ ID NO 20
<211> LENGTH: 36
<212> TYPE: DNA
<213> ORGANISM: Artificial sequence
<220> FEATURE:
<223> OTHER INFORMATION: Primer

<400> SEQUENCE: 20
gtcccagcta gaatgcagaa aataacggct cacagc                                    36

<210> SEQ ID NO 21
<211> LENGTH: 36
<212> TYPE: DNA
<213> ORGANISM: Artificial sequence
<220> FEATURE:
<223> OTHER INFORMATION: Primer

<400> SEQUENCE: 21
gctgtgagcc gttattttct gcattctagc tgggac                                    36
```

MUTANT PNEUMOLYSIN PROTEINS

This application is a §371 application of PCT/GB2005/001792, which in turn claims priority to U.S. Provisional Application 60/569,415 and GB application 0410220.8, each being filed 7 May 2004, the entire disclosures of each of the above-identified applications being incorporated herein by reference.

FIELD OF THE INVENTION

The present invention relates to immunogenic compositions comprising mutant *Streptococcus pneumoniae* pneumolysin proteins. The invention further relates to such proteins and nucleic acids encoding these proteins.

BACKGROUND OF THE INVENTION

*Streptococcus pneumoniae* is an important pathogen, causing invasive diseases such as pneumonia, meningitis and bacteraemia. Even in regions where effective antibiotic therapy is freely available, the mortality rate from pneumococcal pneumonia can be as high as 19% in hospitalised patients. In developing countries, in excess of 3 million children under the age of 5 years die each year from pneumonia, of which *S. pneumoniae* is the commonest causative agent. *S. pneumoniae* also causes less serious, but highly prevalent infections such as otitis media and sinusitis, which have a significant impact on healthcare costs in developed countries. Otitis media is especially important in young children, while sinusitis affects both children and adults.

The heptavalent polysaccharide conjugate vaccine from Wyeth, sold as Prevnar® in the United States and as Prevenar® in the rest of the world, is currently the only effective conjugate vaccine available for protection against *Streptococcus pneumoniae* infection (Kyaw et al, 2002; Hausdorff et al, 2000). The vaccine comprises seven purified *Streptococcus* capsular polysaccharides (serotypes 4, 6B, 9V, 14, 18C, 19F and 23F) out of a possible 90 (Kalin, 1998), each conjugated to a carrier protein. Preparation of such a vaccine is described in U.S. Pat. No. 4,673,574 (Anderson). The protein used for conjugation of the capsular polysaccharides is a diphtheria toxoid, $CRM_{197}$, offering an increase in the immunogenicity of the vaccine in infants (Blum et al, 2000; Katkocin, 2000). However, each serotype of *S. pneumoniae* has a structurally distinct capsular polysaccharide, such that immunization with one serotype tends not to confer protection against the majority of the other serotypes, although some cross-protection does occur against vaccine-related serotypes (Whitney et al., 2003).

Complementary approaches to serotype-specific immunization are being investigated. A possibility is to also use a species-common virulence factor such as Pneumolysin (PLY), the 53 kDa toxin produced by all invasive strains of *S. pneumoniae* (Paton et al, 1993). PLY could be used alone or as a carrier protein conjugated to the polysaccharides in Prevnar®, offering increased efficacy. Alexander et al (1994) demonstrated that immunisation of mice with a PLY toxoid conferred immune protection upon Challenge with 9 different serotypes of *S. pneumoniae*. PLY has been shown to stimulate an immune response similar to that of *S. pneumoniae* infection by activating the classical complement pathway (Paton et al, 1984) and inducing apoptosis of neutrophils and macrophages (Cockeran et al, 2002; Kadioglu et al, 2000).

PLY belongs to the group of Cholesterol-binding Cytolysins (CBCs) that bind to the cholesterol of host cell membranes prior to formation of large 30-50mer ring structures that create lytic pores (Palmer, 2001; Jedrzejas, 2001). The mechanism of pore-formation is not fully understood and there is much debate over the sequence of events (Bonev et al, 2000; Shepard et al, 1998). However, the ability to form pores means that native PLY is highly toxic, which is a problem in terms of the development of immunogenic compositions.

Although the conjugation process used in production would render PLY non-toxic, it would be more favourable to start with a non-toxic form. Further, a toxic form would be difficult to use in preparation of unconjugated immunogenic compositions. The toxicity of PLY can be significantly reduced by site-directed mutagenesis to create PLY toxoids, known as pneumolysoids (Paton, 1996).

A variety of such toxoids exist and have been shown to give immune protection, either independently or when conjugated to polysaccharides, to mice in response to a challenge with virulent type 2 D39 *S. pneumoniae* (Paton et al, 1991; Alexander et al, 1994). Most mutations have previously been created in the highly conserved 11 amino acid region near the C' terminus (Mitchell et al, 1992; Berry et al, 1995). This site has been shown to be involved in binding to the host cell (de los Toyos et air 1996). A number of such mutated forms of PLY are described in International Patent Application WO 90/06951; each of the mutations described in this publication is towards the C' terminus of the protein.

A further problem with PLY is that it aggregates upon large-scale production, a problem which must be solved in order for PLY to be used in immunogenic compositions. It is believed that the aggregation of PLY is related to the oligomerisation of PLY involved in pore formation. The present invention thus attempts to reduce or eliminate PLY-PLY interaction (oligomerisation), such that the chance of aggregation during large-scale production will decrease, thereby creating an easily purified form of PLY.

Toyos et al (1996) describe the raising of monoclonal antibodies (mAbs) to various regions of PLY, and probing of the whole toxin and a 'proteinase K nicked' form. Proteinase K cuts PLY into a 37 kDa and 15 kDa fragment. Antibody mAb PLY 4 only recognised whole PLY, and neither of the fragments, indicating that the epitope on PLY for this mAb is within the nicked region. When PLY was pre-incubated with mAb PLY 4, then added to liposomes, the toxin no longer formed pores on the liposome membrane. This implies that the site blocked by mAb PLY 4 (thought to be the Asparagine $N_{143}$ region) is the site responsible for interaction with other PLY monomers to form oligomeric pores. Oligomerisation of Streptolysin O from *Streptococcus* sp. can also be blocked by mAbs as demonstrated by Hugo et al in 1986. It is unknown whether the antibodies directly prevent oligomerisation by binding to the oligomerisation site or if there is an association that sterically hinders the interaction of toxin monomers.

Monoclonal antibody PLY 4 has been further characterised by Suárez-Álvarez et al (2003) and they suggest that the epitope for mAb PLY 4 is further downstream than the $N_{143}$ region initially proposed by Toyos et al in 1996. The site of recognition now appears to be conformation dependent and within amino acids $E_{151}$-$Y_{247}$ and not within the $N_{143}$ region.

Previously a $N_{142}N_{143}$ deletion and $N_{143}D$ substitution within PLY were created by the present inventors as initial steps to understanding this region and its role in oligomerisation. Characterisation of both mutants revealed identical behaviour to native PLY in terms of haemolysis and pore formation (Search, 2002), suggesting that oligomerisation was not blocked, and the toxicity of the mutants remained unchanged. Thus, previously created mutant PLY forms do not exhibit reduced toxicity or reduced oligomerisation, suggesting that these mutations will not be of assistance in the production of immunogenic compositions.

SUMMARY OF THE INVENTION

The present invention relates broadly to immunogenic compositions comprising mutant *Streptococcus pneumoniae* pneumolysin proteins. The invention further relates to such proteins and nucleic acids encoding these proteins.

Thus, in one aspects the invention is directed to an isolated mutant pneumolysin (PLY) protein, wherein the mutant PLY protein differs from the wild type PLY protein by the presence of a mutation within the region of amino acids 144 to 161 of the wild type sequence, such that the toxicity of the mutant is reduced relative to that of the wild-type protein. The mutation may be located within the region of amino acids 144 to 151 of the wild type sequence.

The mutation may be a deletion or substitution of one or more amino acids within the region of amino acids 144 to 161 of the wild type sequence.

The mutant PLY protein may differ from the wild type protein by the substitution or deletion of one or more amino acids within the region of amino acids 144 to 151 of the wild type sequence.

For example, the mutant PLY protein may differ from the wild type protein by the substitution or deletion of two adjacent amino acids within the region of amino acids 144 to 151 of the wild type sequence, as exemplified by the deletion of amino acids valine 144 and proline 145, alanine 146 and arginine 147, methionine 148 and glutamine 149, or tyrosine 150 and glutamic acid 151.

Any of the foregoing mutant PLY proteins may further comprise at least one amino acid substitution or deletion in at least one of the regions of amino acids 257-297, 367-397 or 424-437 of the wild type sequence.

The isolated mutant PLY protein has reduced toxicity to mammals. This is typically a consequence of having reduced pore-forming activity, which may be associated with reduced haemolytic activity and/or reduced oligomerisation activity, as compared with wild type PLY protein. Desirably, although not necessarily, the mutant PLY protein has reduced oligomerisation activity to facilitate purification and subsequent manipulation.

In a further aspect, the invention is directed to an immunogenic conjugate comprising: (a) a saccharide, oligosaccharide, polysaccharide, peptide, polypeptide or protein; and (b) an Isolated mutant pneumolysin (PLY) protein, wherein the mutant PLY protein differs from the wild type PLY protein by the presence of a mutation within the region of amino acids 144 to 161 of the wild type sequence, such that the toxicity of the mutant is reduced relative to that of the wild-type protein. The mutation may be located within the region of amino acids 144 to 151 of the wild type sequence.

The mutation may be a substitution or deletion of one or more amino acids within the region of amino acids 144 to 161 of the wild type sequence.

The mutant PLY protein of the immunogenic conjugate may differ from the wild type protein by the substitution or deletion of one or more amino acids within the region of amino acids 144 to 151 of the wild type sequence.

For example, the mutant PLY protein of the immunogenic conjugate differs from the wild type protein by the substitution or deletion of two adjacent amino acids within the region of amino acids 144 to 151 of the wild type sequence, as exemplified by the deletion of amino acids valine 144 and proline 145, alanine 146 and arginine 147, methionine 148 and glutamine 149, or tyrosine 150 and glutamic acid 151.

Any of the foregoing mutant PLY proteins of the immunogenic conjugate may further comprise at least one amino acid substitution or deletion in at least one of the regions of amino acids 257-297, 367-397 or 424-437 of the wild type sequence.

The saccharide, oligosaccharide or polysaccharide of the immunogenic conjugate may be derived from *Streptococcus pneumoniae*.

In a further aspect, the invention provides an isolated and purified nucleic acid sequence comprising a nucleic acid sequence a) encoding a mutant pneumolysin (PLY) protein, wherein the mutant PLY protein differs from the wild type PLY protein by the presence of a mutation within the region of amino acids 144 to 161 of the wild type sequence, such that the toxicity of the mutant is reduced relative to that of the wild-type protein; or b) which is complementary to a nucleic acid sequence defined in a).

The mutation may be located within the region of amino acids 144 to 151 of the wild type sequence.

The mutation may be a substitution or deletion of one or more amino acids within the region of amino acids 144 to 161 of the wild type sequence.

The nucleic acid sequence may encode a mutant PLY protein which differs from the wild type protein by the substitution or deletion of one or more amino acids within the region of amino acids 144 to 151 of the wild type sequence.

For example, the nucleic acid sequence may encode a mutant PLY protein which differs from the wild type protein by the substitution or deletion of two adjacent amino acids within the region of amino acids 144 to 151 of the wild type sequence, as exemplified by the substitution or deletion of amino acids valine 144 and proline 145, alanine 146 and arginine 147, methionine 148 and glutamine 149, or tyrosine 150 and glutamic acid 151.

The mutant PLY proteins encoded by the nucleic acid sequence may be any of the foregoing, and may further comprise at least one amino acid substitution or deletion in at least one of the regions of amino acids 257-297, 367-397 or 424-437 of the wild type sequence.

In a still further aspect, the invention provides a recombinant expression vector which comprises any of the foregoing isolated and purified nucleic acid sequences encoding a mutant PLY protein, as well as a recombinant host cell transformed, transfected or infected with such a recombinant expression vector.

In another aspect, the invention provides a method of producing an isolated mutant pneumolysin (PLY) protein of the invention, wherein the mutant PLY protein differs from the wild type PLY protein by the presence of a mutation within the region of amino acids 144 to 161 of the wild type sequence, such that the toxicity of the mutant is reduced relative to that of the wild-type protein, the method comprising: a) transforming, transfecting or infecting a host cell with a recombinant expression vector as described above and culturing the host cell under conditions which permit the expression of said mutant PLY protein by the host cell; and b) recovering the mutant PLY protein from the culture.

In still another aspect, there is provided an immunogenic composition which comprises: a) an isolated mutant pneumolysin (PLY) protein, in unconjugated form or as part of an immunogenic conjugate as described above, wherein the mutant PLY protein differs from the wild type PLY protein by the presence of a mutation within the region of amino acids 144 to 161 of the wild type sequence, such that the toxicity of the mutant is reduced relative to that of the wild-type protein; and b) one or more of a physiologically acceptable adjuvant, diluent or carrier.

The mutation may be located within the region of amino acids 144 to 151 of the wild type sequence.

The mutation may be a substitution or deletion of one or more amino acids within the region of amino acids 144 to 161 of the wild type sequence.

The isolated mutant pneumolysin (PLY) protein of the composition may differ from the wild type PLY protein by the substitution or deletion of one or more amino acids within the region of amino acids 144 to 151 of the wild type sequence.

For example, the mutant PLY protein may differ from the wild type PLY protein by the substitution or deletion of two adjacent amino acids within the region of amino acids 144 to 151 of the wild type sequence, as exemplified by the substitution or deletion of amino acids valine 144 and proline 145, alanine 146 and arginine 147, methionine 148 and glutamine 149, or tyrosine 150 and glutamic acid 151.

The immunogenic composition may contain any of the foregoing mutant PLY proteins, in unconjugated form or as part of an immunogenic conjugate as described above, which further comprises at least one amino acid substitution or deletion in at least one of the regions of amino acids 257-297, 367-397 or 424-437 of the wild type sequence.

Thus, the immunogenic composition may comprise: a) an immunogenic conjugate comprising: (i) a saccharide, oligosaccharide or polysaccharide derived from *Streptococcus*, e.g. *Streptococcus pneumoniae*; and (ii) an isolated mutant pneumolysin (PLY) protein, wherein the mutant PLY protein differs from the wild type PLY protein by the presence of a mutation within the region of amino acids 144 to 161 of the wild type sequence, such that the toxicity of the mutant is reduced relative to that of the wild-type protein; and b) one or more of a physiologically acceptable adjuvant, diluent or carrier. The composition may comprise a plurality of *Streptococcus pneumoniae* subtypes of saccharides, oligosaccharides or polysaccharides.

In further aspects, the invention is directed to a method of prophylaxis for a mammal, the method comprising the step of administering to a subject mammal an immunogenic composition which comprises: a) an isolated mutant pneumolysin (PLY) protein, wherein the mutant PLY protein differs from the wild type PLY protein by the presence of a mutation within the region of amino acids 144 to 161 of the wild type sequence, such that the toxicity of the mutant is reduced relative to that of the wild-type protein; and b) one or more of a physiologically acceptable adjuvant, diluent or carrier.

The immunogenic composition may comprise: a) an immunogenic conjugate comprising: (i) a saccharide, oligosaccharide, polysaccharide, peptide, polypeptide or protein; and (ii) an isolated mutant pneumolysin (PLY) protein as described herein.

In another aspect, the invention is directed to the use of any of the isolated mutant PLY proteins or immunogenic conjugates of the invention in the preparation of an immunogenic composition. The invention also provides a method of preparing an immunogenic composition, comprising the step of admixing a mutant protein or immunogenic conjugate of the invention with a pharmaceutically acceptable carrier.

The immunogenic compositions of the invention may be used for the prophylaxis or treatment of bacterial infection. In particular they are useful for the prophylaxis or treatment of infection by bacteria having cholesterol-binding cytolysins (see e.g. Palmer, 2001) which are immunologically cross reactive with PLY; that is to say, which are capable of being bound by antibodies which will bind to PLY. Preferably though, the bacteria are Streptococci, preferably *Streptococcus pneumoniae*.

In a further aspect, the present invention provides an isolated mutant PLY protein or immunogenic conjugate of the invention for use in a method of medical treatment.

In a still further aspect, the invention is directed to a method of preparation of an immunogenic composition, the method comprising the steps of: providing an isolated mutant PLY protein as described herein; and conjugating the mutant protein to a saccharide, oligosaccharide, polysaccharide, peptide, polypeptide or protein. The mutant protein in the foregoing method may be conjugated to a *Streptococcus pneumoniae* polysaccharide. The method may comprise the further step of admixing the conjugate thus obtained with a pharmaceutically acceptable carrier.

In a further aspect, the invention is directed to a method of screening candidate mutant PLY proteins for suitability for use in immunogenic compositions, the method comprising the steps of: providing a mutant PLY protein; testing the mutant protein for haemolytic activity; testing the mutant PLY protein for oligomerisation activity; and comparing the mutant PLY protein haemolytic and oligomerisation activity with those of a non-mutant protein.

BRIEF DESCRIPTION OF THE FIGURES

FIG. 1 shows the amino acid sequence of wild-type pneumolysin (SEQ ID NO: 1);

DETAILED DESCRIPTION OF THE INVENTION

Figure 2:
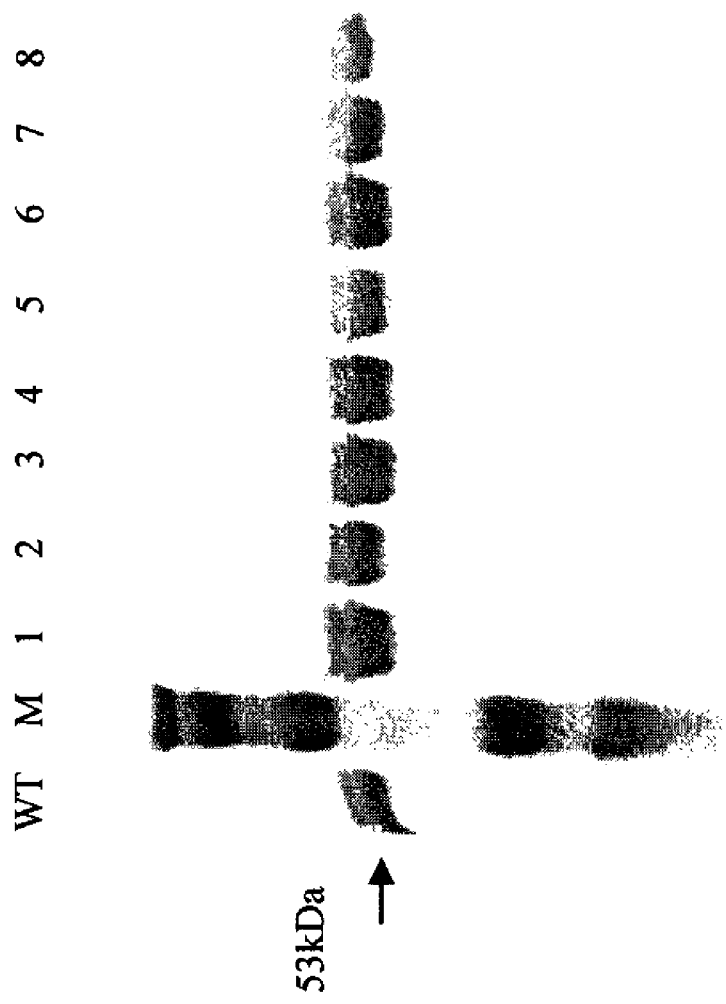
FIG. 2 shows a western blot of PLY deletion mutants detected by mAb PLY4.

PLY is a member of the group of cholesterol-binding cytolysins (CBCs). The amino acid sequence of wild type pneumolysin is given in FIG. 1. FIG. 1 also indicates the GenBank identification number of the sequence, derived from NCBI-GenBank Fiat File Release 141.0, Apr. 15, 2004.

The present invention relies on the identification of a number of PLY forms having a mutation within the region of amino acids 144 to 161 of the wild type PLY protein which have reduced toxicity, as reflected by a reduction in haemolytic activity and/or oligomerisation. The consensus sequence of this region is as follows: VPARMQYEKITAHSMEQL (SEQ ID NO: 2) (see FIG. 1).

In one aspect, the present invention relates to mutant PLY proteins which differ from the wild type protein by the mutation within the region of amino acids 144 to 151 of the wild type sequence. The consensus sequence of this region is as follows: VPARMQYE (SEQ ID NO: 3) (see FIG. 1).

The mutant may have a substitution or deletion of one or more amino acids within the region of amino acids 144 to 161, e.g. 144 to 151.

Thus, in all aspects of the invention, the mutant pneumolysin may have a mutation, e.g. a substitution or deletion, at one or more of amino acids 144, 145, 146, 147, 148, 149, 150, 151, 152, 153, 154, 155, 156, 157, 158, 159, 160 or 161 of the wild type sequence.

The invention further relates to mutant PLY proteins which differ from the wild type protein by the substitution or deletion of two adjacent amino acids within the region of amino acids 144 to 151 of the wild type sequence. Examples of such double mutants are those which contain substitutions or deletions of amino acids valine 144 and proline 145, alanine 146 and arginine 147, methionine 148 and glutamine 149, or tyrosine 150 and glutamic acid 151.

These mutant PLY proteins are used per se in immunogenic compositions, together with one or more of a physiologically acceptable adjuvant, diluent or carrier.

Alternatively, these mutant PLY proteins are conjugated to a saccharide, oligosaccharide, polysaccharide, peptide, polypeptide or protein, from the same or heterologous organism, to form conjugates which are used in immunogenic compositions, together with one or more of a physiologically acceptable adjuvant, diluent or carrier. Thus the saccharide, oligosaccharide, polysaccharide, peptide, polypeptide or protein to which the mutant PLY is conjugated may be from *Streptococcus*, e.g. *Streptococcus pneumoniae*. They may be derived from the bacterial capsule.

In either unconjugated or conjugated form, the mutant PLY proteins contained in immunogenic compositions are used in prophylaxis or therapy.

In either unconjugated or conjugated form, the mutant PLY proteins may further contain at least one amino acid substitution or deletion in at least one of the regions of amino acids 257-297, 367-397 or 424-437 of the wild type sequence.

These further substitutions or deletions are described in Paton et al. published International Patent Application WO 90/06951.

According to a further aspect of the present invention, there is provided an immunogenic composition comprising an isolated mutant PLY protein as described herein. In one embodiment, the immunogenic composition is a *Streptococcus pneumoniae* immunogenic composition.

The mutant PLY proteins may retain immunogenic activity in mammals. By "immunogenic in mammals" is meant that mammalian immune systems will produce antibodies to the mutant PLY protein, and that these antibodies will also recognise wild type PLY protein. Similarly, mammalian antibodies to the wild type PLY protein will also recognise the mutant PLY protein. Preferably the mutant protein is immunogenic in humans. Preferably the mutant PLY protein will stimulate the mammalian immune system to produce antibodies which bind to the wild type VPARMQYEKITAHSMEQL (SEQ ID NO: 2) or VPARMQYE (SEQ ID NO: 3) sequence.

In one embodiment, the mutation is in the region of the PLY protein involved in oligomerisation of the wild type protein.

Without being bound by theory, it is believed that the mutant PLY protein has reduced toxicity as a result of reduced pore-formation activity compared with wild type PLY protein. This is believed to be associated with reduced oligomerisation activity and/or reduced haemolytic activity. Toxicity may be measured directly. Alternatively, one or more of pore formation, oligomerisation and haemolysis may be measured to provide an indication of likely toxicity.

Deletions and substitutions are examples of mutations which may be used to provide the PLY mutant proteins with reduced toxicity. Non-conservative substitutions may be particularly suitable for reducing toxicity of the PLY mutant, as a mutant having a non-conservative mutation is less likely to retain wild-type levels of function than one having a conservative substitution.

A conservative substitution may be defined as a substitution within an amino acid class and/or a substitution that scores positive in the BLOSUM62 matrix as shown below, thus a non-conservative substitution may be defined as a substitution between amino acid classes, or which does not score positive in the BLOSUM62 matrix.

According to one classification, the amino acid classes are acidic, basic, uncharged polar and nonpolar, wherein acidic amino acids are Asp and Glu; basic amino acids are Arg, Lys and His; uncharged polar amino acids are Asn, Gln, Ser, Thr and Tyr; and non-polar amino acids are Ala, Gly, Val, Leu, Ile, Pro, Phe, Met, Trp and Cys.

According to another classification, the amino acid classes are small hydrophilic, acid/acidamide/hydrophilic, basic, small hydrophobic and aromatic, wherein small hydrophilic amino acids are Ser, Thr, Pro, Ala and Gly; acid/acidamide/hydrophilic amino acids are Asn, Asp, Glu and Gln; basic amino acids are His, Arg and Lys; small hydrophobic amino acids are Met, Ile, Leu and Val; and aromatic amino acids are Phe, Tyr and Trp.

Conservative substitutions, which score positive in the BLOSUM62 matrix, are as follows:

| Original Residue | C | S | T | P | A | G | N | D | E | Q | H | R | K | M | I | L | V | F | Y | W |
|---|---|---|---|---|---|---|---|---|---|---|---|---|---|---|---|---|---|---|---|---|
| Substitution | — | T | S | — | S | — | S | N | D | E | N | Q | E | I | M | M | M | Y | H | F |
|  |  | A |  |  |  |  | D | E | Q | R | Y | K | Q | L | L | I | I | W | F | Y |
|  |  | N |  |  |  |  | H |  | K | K |  | R |  | V | V | V | L |  | W |  |

The mutant pneumolysin protein of the invention preferably has at least 80% amino acid identity with the wild type sequence as shown in FIG. 1. The mutant may have at least 85% identity, at least 90% identity, or at least 95% identity with the wild type sequence.

Percent (%) amino acid sequence identity with respect to a reference sequence is defined as the percentage of amino acid residues in a candidate sequence that are identical with the amino acid residues in the reference sequence, after aligning the sequences and introducing gaps, if necessary, to achieve the maximum percent sequence identity, and not considering any conservative substitutions as part of the sequence identity. % identity values may be determined by WU-BLAST-2 (Altschul et al., Methods in Enzymology, 266:460-480 (1996)). WU-BLAST-2 uses several search parameters, most of which are set to the default values. The adjustable parameters are set with the following values: overlap span 1, overlap fraction=0.125, word threshold (T)=11. A % amino acid sequence identity value is determined by the number of matching identical residues as determined by WU-BLAST-2, divided by the total number of residues of the reference sequence (gaps introduced by WU-BLAST-2 into the reference sequence to maximize the alignment score being ignored), multiplied by 100.

Percent (%) amino acid similarity is defined in the same way as identity, with the exception that residues scoring a positive value in the BLOSUM62 matrix are counted. Thus, residues which are non-identical but which have similar properties (e.g. as a result of conservative substitutions) are also counted.

Amino acid insertions within the region of amino acids 144 to 161, e.g. 144 to 151, may also be used to reduce toxicity of the PLY mutant. For example, insertions of 1, 2, 3, 4, 5, 10, 15, 20 or more amino acids may be used. However, deletions and substitutions are generally preferred to insertions as they are less likely to disrupt the wild type epitope; such disruption could reduce the immunogenicity of the mutant protein, which may be undesirable in an immunogenic composition.

In another aspect of the present invention, the mutant PLY protein is conjugated to a saccharide, oligosaccharide, polysaccharide, peptide, polypeptide or protein to form an immunogenic conjugate. In this aspect, the mutant PLY protein may retain its immunogenicity, or that immunogenicity may be ablated. In either event, the mutant PLY protein serves to enhance the immunogenicity of the saccharide, oligosaccharide, polysaccharide, peptide, polypeptide or protein in the conjugate.

Such saccharides, oligosaccharides, polysaccharides, peptides, polypeptides or proteins are each conjugated to the mutant PLY protein in any suitable manner, including, but not limited to: (1) direct coupling via protein functional groups (e.g., thiol-thiol linkage, amine-carboxyl linkage, amine-aldehyde linkage; enzyme direct coupling); (2) homobifunctional coupling of amines (e.g., using bis-aldehydes); (3) homobifunctional coupling of thiols (e.g., using bis-maleimides); (4) homobifunctional coupling via photoactivated reagents (5) heterobifunctional coupling of amines to thiols (e.g., using maleimides); (6) heterobifunctional coupling via photoactivated reagents (e.g., the β-carbonyldiazo family); (7) introducing amine-reactive groups into a poly- or oligosaccharide via cyanogen bromide activation or carboxymethylation; (8) introducing thiol-reactive groups into a poly- or oligosaccharide via a heterobifunctional compound such as maleimido-hydrazide; (9) protein-lipid conjugation via introducing a hydrophobic group into the protein and (10) protein-lipid conjugation via incorporating a reactive group into the lipid. Also, contemplated are heterobifunctional "non-covalent coupling" techniques such as the Biotin-Avidin interaction. For a comprehensive review of conjugation techniques, see Aslam and Dent (1998), incorporated hereinafter by reference in its entirety.

Further methods of conjugating a peptide, polypeptide or protein to a protein are described in U.S. provisional patent applications 60/530,480 and 60/530,481, both filed Dec. 17, 2003, and both incorporated by reference in their entirety.

Additionally, U.S. Pat. No. 5,565,204 to Kuo et al. described a method for conjugating such polysaccharides to the wild type PLY protein; that method is also suitable for conjugating such polysaccharides to the mutant PLY proteins of this invention.

The immunogenic compositions of the present invention may be conjugated immunogenic compositions. Each immunogenic composition may comprise one or more saccharides, oligosaccharides, polysaccharides, peptides, polypeptides or proteins, which may be derived from the source organism (*S. pneumoniae*) of the wild type PLY protein. In non-limiting examples, such components may be derived from the capsule of the organism.

In one embodiment, the saccharides, oligosaccharides or polysaccharides are derived from more than one serotype of *S. pneumoniae*; the particular serotypes will depend on the intended use for the immunogenic composition and the prevalence of these serotypes in the target population.

Alternatively, the saccharides, oligosaccharides, polysaccharides, peptides, polypeptides or proteins are derived from a heterologous organism (that is, an organism other than *S. pneumoniae*). In the case of saccharides, oligosaccharides or polysaccharides, multiple serotypes may be obtained from, without limitation, *Neisseria meningitidis* (for example, from serotypes A, C, Y and W135), *Staphylococcus aureus* and *Haemophilus influenzae*.

In certain aspects of the invention, the mutant PLY protein is conjugated to another peptide, polypeptide or protein of *S. pneumoniae*. Alternatively, the mutant PLY protein is conjugated to a peptide, polypeptide or protein from a heterologous organism, including a human. For example, the mutant PLY protein is conjugated to another peptide, polypeptide or protein, which is from a pathogenic virus, bacterium, fungus or parasite, or (2) from a cancer cell or tumor cell, or (3) from an allergen so as to interfere with the production of IgE so as to moderate allergic responses to the allergen, or (4) from amyloid precursor protein (APP) so as to prevent or treat disease characterized by amyloid deposition in a vertebrate host.

The moiety of APP which is conjugated to the mutant PLY protein may be the β-amyloid peptide (also referred to as Aβ peptide), which is an internal, 39-43 amino acid fragment of (APP), which is generated by processing of APP by the β and γ secretase enzymes. An example of such a peptide is the Aβ1-42 peptide, which has the following amino acid sequence:

Asp Ala Glu Phe Arg His Asp Ser Gly Tyr Glu Val

His His Gln Lys Leu Val Phe Phe Ala Glu Asp Val

Gly Ser Asn Lys Gly Ala Ile Ile Gly Leu Met Val

Gly Gly Val Val Ile Ala (SEQ ID NO: 4).

The Aβ component may be further administered in the form of a fragment conjugated to the mutant PLY protein. Non-limiting examples of such fragments include Aβ1-3, 1-4, 1-5, 1-6, 1-7, 3-7, 3-8, 3-9, 3-10, 3-11, 1-10 and 1-12. The use of Aβ and fragments thereof, as conjugated to proteins other than PLY, is described in published International Patent Applications WO 99/27944 and WO 00/72880, which are hereby incorporated by reference.

A further aspect of the present invention provides a method of prophylaxis or treatment for a mammal, the method comprising the step of administering to a subject mammal an immunogenic composition comprising an isolated PLY protein having a mutation as described herein, where the mutant PLY protein is unconjugated or conjugated as described herein. Typically the method is intended for prophylaxis or treatment of infection by one or more species or strains of bacteria having a cholesterol-binding cytolysin which is immunologically cross-reactive with wild-type pneumolysin, particularly *Streptococcus*, and in particular, *Streptococcus pneumoniae*. Other species, and their cytolysins, include *Clostridium perfringens* (Perfringolysin O), *Streptococcus intermedius* (Intermedilysin), *Bacillus alvei* (Alveolysin), *Bacillus anthracis* (Anthrolysin), *Bacillus cereus* (Cereolysin), *Listeria ivanovii* (Ivanolysin O), *Clostridium novyi* (Novyilisin), *Arcanobacterium pyogenes* (Pyolysin), *Listeria seeligeri* (Seeligeriolysin O), *Clostridium septicum* (Septicolysin), *S. pyogenes* (Streptolysin O), *Streptococcus suis* (Suilysin), *Clostridium tetani* (Tetanolysin) *Listeria monocytogenes* (Listeriolysin O), *Streptococcus equisimilis* (Streptolysin O), *S. canis* (Streptolysin O), *Bacillus thuringiensis* (Thuringiolysin O), *B. laterosporus* (Latersporolysin O), *Clostridium botulinum* (Botulinolysin), *C. chauvoei* (Chauveolysin), *C. bifermentans* (Bifermentolysin), *C. sordellii* (Sordellilysin) (see e.g. Palmer 2001).

The mode of administration of an immunogenic composition of the invention, whether of the mutant PLY protein alone or as part of an immunogenic conjugate, may be by any suitable route which delivers an immunoprotective amount of the protein to the subject. One such route is the parenteral route, such as by intramuscular or subcutaneous administration. Other modes of administration may also be employed, where desired, such as the mucosal route, such as by oral, rectal, buccal or intranasal administration, or via other parenteral routes, i.e., intradermally or intravenously.

Generally, the immunogenic composition will usually be presented as a pharmaceutical formulation including a physiologically acceptable carrier or excipient, for example, sterile water or sterile isotonic saline, as well as any and all solvents, dispersion media, coatings, antibacterial and antifungal agents, isotonic and absorption delaying agents, and the like, compatible with administration to humans. The appropriate carrier will be evident to those skilled in the art and will depend in large part upon the route of administration. The immunogenic composition of the present invention may also include a physiologically acceptable diluent such as sterile water or sterile isotonic saline. The formulation may be prepared by conventional means.

It will be understood, however, that the specific dose level for any particular recipient mammal will depend upon a variety of factors including age, general health, and sex; the time of administration; the route of administration; synergistic effects with any other drugs being administered; and the degree of protection being sought. Of course, the administration can be repeated at suitable intervals if necessary.

The mammal may be a human, or may be a non-human mammal. The immunogenic composition may be administered in any convenient manner; for example, those described above.

The immunogenic composition of the present invention may include one or more physiologically acceptable adjuvants. A substance that enhances the immune response when administered together with an immunogen or antigen is known as an adjuvant. A number of cytokines or lymphokines have been shown to have immune modulating activity, and thus may be used as adjuvants, including, but not limited to, the interleukins 1-α, 1-β, 2, 4, 5, 6, 7, 8, 10, 12 (see, e.g., U.S. Pat. No. 5,723,127, which is hereby incorporated by reference), 13, 14, 15, 16, 17 and 18 (and its mutant forms), the interferons-α, β and γ, granulocyte-macrophage colony stimulating factor (GM-CSF; see, e.g., U.S. Pat. No. 5,078,996, which is hereby incorporated by reference, and ATCC Accession Number 39900), macrophage colony stimulating factor (M-CSF), granulocyte colony stimulating factor (G-CSF), and the tumor necrosis factors α and β. Still other adjuvants useful in this invention include a chemokine, including without limitation, MCP-1, MIP-1α, MIP-1β, and RANTES. Adhesion molecules, such as a selectin, e.g., L-selectin, P-selectin and E-selectin may also be useful as adjuvants. Still other useful adjuvants include, without limitation, a mucin-like molecule, e.g., CD34, GlyCAM-1 and MadCAM-1, a member of the integrin family such as LFA-1, VLA-1, Mac-1 and p150.95, a member of the immunoglobulin superfamily such as PECAM, ICAMs, e.g., ICAM-1, ICAM-2 and ICAM-3, CD2 and LFA-3, co-stimulatory molecules such as CD40 and CD40L, growth factors including vascular growth factor, nerve growth factor, fibroblast growth factor, epidermal growth factor, B7.2, PDGF, BL-1, and vascular endothelial growth factor, receptor molecules including Fas, TNF receptor, Flt, Apo-1, p55, WSL-1, DR3, TRAMP, Apo-3, AIR, LARD, NGRF, DR4, DR5, KILLER, TRAIL-R2, TRICK2, and DR6. Still another adjuvant molecule includes Caspase (ICE). See, also International Patent Publication Nos. WO98/17799 and WO99/43839, incorporated herein by reference.

Suitable adjuvants used to enhance an immune response further include, without limitation, MPL™ (3-O-deacylated monophosphoryl lipid A; Corixa, Hamilton, Mont.), which is described in U.S. Pat. No. 4,912,094, which is hereby incorporated by reference. Also suitable for use as adjuvants are synthetic lipid A analogs or aminoalkyl glucosamine phosphate compounds (AGP), or derivatives or analogs thereof, which are available from Corixa (Hamilton, Mont.), and which are described in U.S. Pat. No. 6,113,918, which is hereby incorporated by reference. One such AGP is 2-[(R)-3-Tetradecanoyloxytetradecanoylamino]ethyl 2-Deoxy-4-O-phosphono-3-O—[(R)-3-tetradecanoyoxytetradecanoyl]-2-[(R)-3-tetradecanoyloxytetradecanoyl-amino]-β-D-glucopyranoside, which is also known as 529 (formerly known as RC529). This 529 adjuvant is formulated as an aqueous form or as a stable emulsion.

Still other adjuvants include mineral oil and water emulsions, aluminum salts (alum), such as aluminum hydroxide, aluminum phosphate, etc., Amphigen, Avridine, L121/squalene, D-lactide-polylactide/glycoside, pluronic polyols, muramyl dipeptide, killed *Bordetella*, saponins, such as Stimulon™ QS-21 (Antigenics, Framingham, Mass.), described in U.S. Pat. No. 5,057,540, which is hereby incorporated by reference, and particles generated therefrom such as ISCOMS (immunostimulating complexes), *Mycobacterium tuberculosis*, bacterial lipopolysaccharides, synthetic polynucleotides such as oligonucleotides containing a CpG motif (U.S. Pat. No. 6,207,646, which is hereby incorporated by reference), a pertussis toxin (PT), or an *E. coli* heat-labile toxin (LT), particularly LT-K63, LT-R72, PT-K9/G129; see, e.g., International Patent Publication Nos. WO 93/13302 and WO 92/19265, incorporated herein by reference.

Also useful as adjuvants are cholera toxins and mutants thereof, including those described in published International Patent Application number WO 00/18434 (wherein the glutamic acid at amino acid position 29 is replaced by another amino acid (other than aspartic acid), preferably a histidine). Similar CT toxins or mutants are described in published International Patent Application number WO 02/098368 (wherein the isoleucine at amino acid position 16 is replaced by another amino acid, either alone or in combination with the replacement of the serine at amino acid position 68 by another amino acid; and/or wherein the valine at amino acid position 72 is replaced by another amino acid). Other CT toxins are described in published International Patent Application number WO 02/098369 (wherein the arginine at amino acid position 25 is replaced by another amino acid; and/or an amino acid is inserted at amino acid position 49; and/or two amino acids are inserted at amino acid positions 35 and 36).

The haemolytic activity of the mutant PLY protein may be determined in any suitable manner. One particular protocol as used in the present invention is as follows. Toxin was prepared in serial dilutions in 1.5 ml 1×PBS (Oxoid). An equal volume of 2% (vol/vol) SRBC (sheep red blood cell) was added to each dilution and incubated at 37° C. for 30 minutes. Solutions were then centrifuged at 3000 rpm for 5 minutes to pellet SRBC membranes or whole cells. Haemoglobin content of the supernatant was read at OD540 nm and plotted against toxin concentration to give the degree of haemolysis in relation to toxin concentration. An OD540 nm of 0.5=50% lysis.

Preferably the mutant protein is non-haemolytic at concentrations of more than 1 μg/ml; more preferably at concentrations of more than 5 μg/ml, still more preferably at more than 10 μg/ml, at more than 25 μg/ml, or at more than 35 μg/ml; and most preferably at more than 50 μg/ml. Determination of haemolysis may be carried out as described above.

Determination of pore-forming activity may be determined in any suitable manner; a preferred protocol relies on visual inspection of SRBC membranes by means of electron microscopy; this allows the number of pores to be visualised. This protocol is described in more detail below.

Several methods may be employed to analyse oligomerising activity of pore-forming toxins. For example, analytical ultracentrifugation, as described by Morgan et al (1993), can be used to study oligomerisation of toxins in solution. A sucrose density gradient can be applied to toxin bound erythrocytes in which oligomers are observed in the high molecular weight fractions and separated from other erythrocyte membrane proteins (Bhakdi et al, 1985; Saunders et al, 1989).

One particular method of comparing the oligomerisation activity of mutant PLY in solution with that of wild type PLY is to use a fluorescence assay conducted in a similar manner to that described by Search (2002). Briefly, ANS (8-anilino-1-napthalene-sulphonic acid) (Kodak Ltd.) binds as an extrinsic fluor to PLY. In aqueous solution, ANS has weak fluorescence at 490 nm (read with JASCO FP-750 spectrofluorometer) but in a hydrophobic environment ANS fluorescence increases. This phenomenon allows the movement of ANS bound PLY monomers to be tracked in solution. Sodium deoxycholate (BDH Laboratory supplies) can be used to induce oligomerisation of pneumolysin. An increase in fluorescence is observed when wild type PLY plus ANS is treated with sodium deoxycholate as the toxin self-associates bringing the ANS from a hydrophilic to hydrophobic environment. Derivatised PLY, that is PLY chemically modified with dithio(bis) nitrobenzoate to remain monomeric, does not result in an increase in fluorescence at 490 nm when treated with sodium deoxycholate. From this experiment, it is predicted that mutant PLY would give the same result as derivatised PLY if it remains monomeric. If mutant PLY is found to fluoresce to the same extent as WT PLY then it can be concluded that mutant PLY does oligomerise.

The toxicity of the proteins and compositions of the invention may be determined directly, by administering the mutant to a non-human test mammal, e.g. a rodent. The toxicity of the mutant may be compared with that of the wild type protein. Suitable indicators of toxicity include survival, animal behaviour, and inflammation (which may be determined by measuring inflammatory cytokine production, e.g. in bronchoalveolar lavage). Suitable protocols are described below in the Examples.

The present invention further provides a method of preparation of an immunogenic composition, the method comprising the steps of:

providing an isolated mutant PLY protein with the mutations described herein and having reduced haemolytic activity compared with wild type PLY protein, the mutant protein being antigenic in mammals; and conjugating the mutant protein to a saccharide, oligosaccharide, polysaccharide, peptide, polypeptide or protein.

According to a further aspect of the present invention, there is provided an isolated and purified nucleic acid sequence comprising an isolated nucleic acid sequence encoding a mutant pneumolysin (PLY) protein wherein the mutant PLY protein differs from the wild type PLY protein by the presence of a mutation within the region of amino acids 144 to 161 of the wild type sequence, such that the toxicity of the mutant is reduced relative to that of the wild-type protein, or which is complementary to such a nucleic acid sequence, the mutant protein being immunogenic in mammals. Further aspects of the invention provide nucleic acid sequences which are complementary to such sequences.

Nucleic acid sequences can be derived from protein sequences based on the degeneracy of the genetic code.

Nucleic acid sequences of the present invention may comprise additional regulatory sequences, for example, promoters or repressors. The nucleic acid sequences may be comprised in an expression vector, for example, plasmids, artificial chromosomes, expression cassettes and the like.

According to a still further aspect of the present invention, there is provided a recombinant host cell transformed, transfected or infected with a recombinant expression vector comprising an isolated and purified nucleic acid sequence expressing a mutant PLY protein as described herein. In one embodiment, the cell is a prokaryotic cell.

According to a still further aspect of the present invention, there is provided a method of screening candidate mutant PLY proteins for suitability for use in immunogenic compositions, the method comprising the steps of:

providing a mutant PLY protein;

testing the mutant protein for haemolytic activity;

testing the mutant protein for oligomerisation activity; and comparing the mutant protein haemolytic and oligomerisation activity with those of a non-mutant protein.

Those mutant proteins which have reduced haemolytic and oligomerisation activity compared with the non-mutant form of the protein will be likely to be good candidates for the preparation of immunogenic compositions.

The method may further comprise the step of testing the mutant protein for immunogenic activity in a target mammal. This may comprise the step of contacting the mutant protein with an antibody to the non-mutant protein. This may be performed in vivo or in vitro.

The invention described herein relates to deletion mutants of pneumolysin which exhibit reduced toxicity, haemolysis and pore formation. The data demonstrate that at 7 μg/dose, Δ6 PLY is not detrimental to mice compared to 2 μg/dose of WT PLY.

Nevertheless, various mutations created by the present inventors surrounding the $N_{143}$ residue and described herein are still recognised by Western blotting with mAb PLY 4, indicating that this highly antigenic site on PLY has not been altered. The site of mutation has been shown to be highly antigenic by epitope scanning and is recognised by both human sera and rabbit hyper-immune sera (Salo et al, 1993).

All mutants created were confirmed to be forms of pneumolysin. The fact that mAb PLY4 recognises the mutants indicates that the epitope has not been altered to such an extent that it is no longer specific for this antibody. Larger deletions within this area should create mutants that are not recognised by mAbPLY4. As this region has been identified as being highly immunogenic (Salo et al, 1993) it is useful that the site remains intact in the deletions that we have created in terms of use in immunogenic compositions.

The non-toxic mutants described herein are within the site proposed to be involved in oligomerisation (de los Toyos et al, 1996). Further in vitro characterisation of one purified toxoid, Δ6 PLY, revealed that it was not cytotoxic to murine fibroblasts or erythrocytes. This suggests that host cell membranes are not lysed by Δ6 PLY because oligomerisation (pore formation) has been prevented. Pores on SRBC membranes treated with WT PLY are readily visible, but pores have not been observed on membranes treated with Δ6 PLY. There were difficulties in fixing Δ6 PLY treated membranes to the grids for visualisation with the EM. This may be due to the agglutination of membranes that are seen in haemolytic assays with Δ6 PLY. The haemagglutination effect observed in haemolytic assays of Δ6 PLY with SRBC suggests that Δ6 PLY monomers still bind to host cell membranes. A labelled form of Δ6 PLY was created which allows visualisation of binding to host cell membranes. From binding assays (data not shown) it was confirmed that Δ6 PLY did bind to the host cell membrane. There may be a weak affinity between the Δ6 PLY monomers, allowing cross-linking of monomers but not formation of true oligomers. This cross-linking of Δ6 PLY monomers in addition to monomers binding to erythrocytes could create the matrix observed in 96-well plates. It is proposed that by creating the Δ6 PLY mutant, the oligomerisation stage was blocked, but host cell binding/recognition was not abolished.

This hypothesis is supported by the finding that Δ146 PLY is still capable of associating with cell membranes as determined using eGFP-tagged versions of the mutant and wild type proteins, but that Δ146 PLY does not form pores in cell membranes. Instead, long chains of protein are seen at the cell surface, which may be self-associated protein which is unable to oligomerise correctly to form pores.

In vivo treatment with Δ6 PLY did not result in an increase of the inflammatory cytokine IL-6 24 hours post-treatment. Mice treated with WT PLY were found to produce 10 times more IL-6 than the saline control and Δ6 PLY treatment. The data established that treatment with Δ6 PLY did not induce the inflammatory side effects that are associated with native PLY. WT PLY treatment resulted in a localised inflammatory response at the site of administration. This localised IL-6 production in the bronchoalveolar lavage is likely to be from recruited neutrophils (Kadioglu, 2000) and alveolar macrophages that produce more IL-6 than the epithelial cells of the lung tissue (Kerr, personal communication 2003).

Wild type PLY severely damaged lung integrity, but lungs treated with Δ6 PLY remained healthy. The large amount of total protein observed in the airways of WT PLY treated mice has been characterised as an influx of host proteins (Rubins & Janoff, 1998). PLY has previously been implicated in the disruption of tight junctions (Rayner et al, 1995), allowing host proteins to 'leak' into the airways via the disruption of the capillary/airway barrier. A low inflammatory response and no disruption to the lungs by Δ6 PLY correlate with Δ6 PLYs inability to create pore-forming oligomers in host cell membranes.

Treatment of mice with WT PLY has also been demonstrated to cause a sustained hypothermic response which is not seen in animals treated with Δ146 PLY.

These and other aspects of the present invention will now be described by way of the following non-limiting examples, and with reference to the accompanying Figures.

EXAMPLES

Example 1

Site-Directed Mutagenesis of Pneumolysin

Eight double amino acid deletions from wild type pneumolysin were created using the Quikchange® site directed mutagenesis kit (Stratagene). The template plasmid was the high expression vector pKK233-3 (Clontech Laboratories) in which PLY was previously inserted. Primers designed to delete the relevant amino acids (see Table 1 below) were ordered from Sigma-Genosys. The following deletions were created to span the $N_{143}$ region of PLY: $W_{134}H_{135}Q_{136}D_{137}Y_{138}G_{139}Q_{140}V_{141}N_{142}N_{143}V_{144}P_{145}$-$A_{146}R_{147}M_{148}Q_{149}Y_{150}E_{151}$ (SEQ ID NO: 5); where (Δ1) $W_{134}H_{135}$ (Δ2) $Q_{136}D_{137}$ (Δ3) $Y_{138}G_{139}$ (Δ4) $Q_{140}V_{141}$, (Δ5) $V_{144}P_{145}$ (Δ6) $A_{146}R_{147}$ (Δ7) $M_{148}Q_{149}$ (Δ8) $Y_{150}E_{151}$ (see Table 2). $N_{142}N_{143}$ was the deletion previously created (Search (2000)), where proteinase K cuts PLY into two fragments.

TABLE 1

Primers used to create double amino acid deletions within the PLY gene

| Primers | Nucleotide sequences of primers for site-directed mutagenesis |
|---|---|
| Δ1 fwd | 5'-CGATTTGTTGGCTAAGCAAGATTATGGTCAGG-3' (SEQ ID NO: 6) |
| Δ1 rev | 5'-CCTGACCATAATCTTGCTTAGCCAACAAATCG-3' (SEQ ID NO: 7) |
| Δ2 fwd | 5'-GTTGGCTAAGTGGCATTATGGTCAGGTCAATAATGTCCC-3' (SEQ ID NO: 8) |
| Δ2 rev | 5'-GGGACATTATTGACCTGACCATAATGCCACTTAGCCAAC-3' (SEQ ID NO: 9) |
| Δ3 fwd | 5'-GGCTAAGTGGCATCAAGATCAGGTCAATAATGTCCC-3' (SEQ ID NO: 10) |
| Δ3 rev | 5'-GGGACATTATTGACCTGATCTTGATGCCACTTAGCC-3' (SEQ ID NO: 11) |
| Δ4 fwd | 5'-GGCATCAAGATTATGGTAATAATGTCCCAGCTAG-3' (SEQ ID NO: 12) |
| Δ4 rev | 5'-CTAGCTGGGACATTATTACCATAATCTTGATGCC-3' (SEQ ID NO: 13) |
| Δ5 fwd | 5'-GGTCAGGTCAATAATGCTAGAATGCAGTATG-3' (SEQ ID NO: 14) |
| Δ5 rev | 5'-CATACTGCATTCTAGCATTATTGACCTGACC-3' (SEQ ID NO: 15) |
| Δ6 fwd | 5'-GGTCAATAATGTCCCAATGCAGTATGAAAAAATAACGGCTC-3' (SEQ ID NO: 16) |
| Δ6 rev | 5'-GAGCCGTTATTTTTTCATACTGCATTGGGACATTATTGACC-3' (SEQ ID NO: 17) |
| Δ7 fwd | 5'-GGTCAATAATGTCCCAGCTAGATATGAAAAAATAACGGCTC-3' (SEQ ID NO: 18) |
| Δ7 rev | 5'-GAGCCGTTATTTTTTCATATCTAGCTGGGACATTATTGACC-3' (SEQ ID NO: 19) |

TABLE 1-continued

Primers used to create double amino acid
deletions within the PLY gene

| Primers | Nucleotide sequences of primers for site-directed mutagenesis |
|---|---|
| Δ8 fwd | 5'-GTCCCAGCTAGAATGCAGAAAATAACGGCTCACAGC-3' (SEQ ID NO: 20) |
| Δ8 rev | 5'-GCTGTGAGCCGTTATTTTCTGCATTCTAGCTGGGAC-3' (SEQ ID NO: 21) |

Note
Reverse primers [rev] are the exact complement and reverse of the forward [fwd] primers with the bases to be deleted removed from the primer.

TABLE 2

Bases deleted for each mutation within the PLY gene and amino acids deleted.

| Deletion | Bases deleted within the PLY gene | Amino acids deleted |
|---|---|---|
| Δ1 | TGGCAT (bp400-405) | $W_{134}H_{135}$ |
| Δ2 | CAAGAT (bp406-411) | $Q_{136}D_{137}$ |
| Δ3 | TATGGT (bp412-417) | $Y_{138}G_{139}$ |
| Δ4 | GAGGTC (bp418-423) | $Q_{140}V_{141}$ |
| Δ5 | GTCCCA (bp430-435) | $V_{144}P_{145}$ |
| Δ6 | GCTAGA (bp436-441) | $A_{146}R_{147}$ |
| Δ7 | ATGCAG (bp442-447) | $M_{148}Q_{149}$ |
| Δ8 | TATGAA (bp448-453) | $Y_{150}E_{151}$ |

Example 2

Protein Expression and Purification

Wild type (WT) and mutant PLY was expressed in *Escherichia coli* and harvested as described previously (Mitchell et al, 1989). Cells were disrupted using the benchtop cell disrupter (Constant Systems Ltd) and cytoplasmic proteins obtained by centrifugation at 13,000 rpm for 30 minutes. Hydrophobic Interaction Chromatography with a phenyl ether matrix (PE20, Applied Biosystems) was used to purify PLY with the BioCAD® 700E Perfusion Chromatography Workstation (Applied Biosystems). Eluted fractions were run on SDS-PAGE and coomassie stained using standard protocol and fractions containing pure PLY were pooled.

Example 3

Quantitative Haemolytic Assay

Haemolytic activity of purified protein was assessed using an assay based on that reported by Walker et al., (1987) using a 2% (vol/vol) sheep red blood cell (SRBC) (E & O laboratories) solution in 1× Phosphate Buffered Saline (PBS) (Oxoid). Pooled fractions were concentrated using minicon B15 clinical sample concentrators (Millipore). Toxin was prepared in serial dilutions in 1.5 ml 1×PBS (Oxoid). An equal volume of 2% (vol/vol) SRBC was added to each dilution and incubated at 37° C. for 30 minutes. Solutions were then centrifuged at 300 rpm for 5 minutes to pellet SRBC membranes or whole cells. Haemoglobin content of the supernatant was read at OD540 nm and plotted against toxin concentration to give the degree of haemolysis in relation to toxin concentration. An OD540 nm of 0.5=50% lysis.

Figure 3:
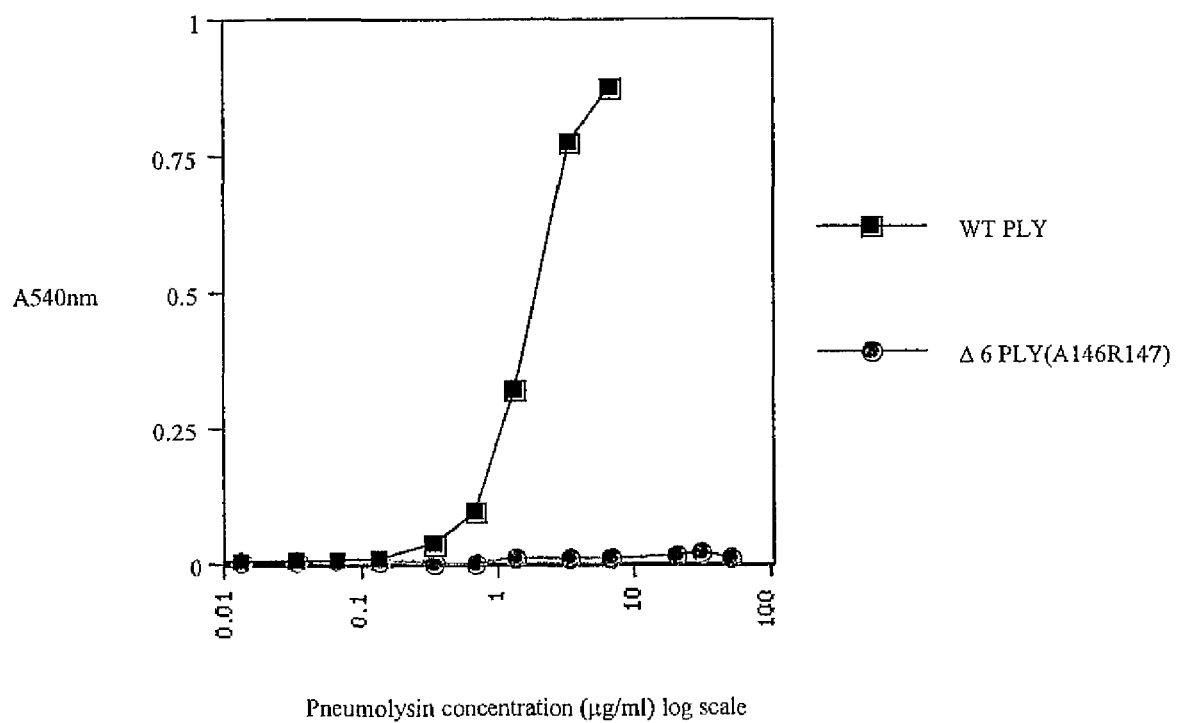
FIG. 3 shows the results of a quantitative haemolytic assay comparing WT PLY to Δ6 PLY mutant.

Crude haemolytic analysis revealed that four of these mutants, deletions 5-8, were non-haemolytic. Further analysis of purified Δ6 PLY ($A_{146}R_{147}$) in a quantitative haemolytic assay (FIG. 3) revealed that it was non-lytic at concentrations of 50 μg/ml whereas <1 μg/ml of WT PLY was haemolytic to SRBC. Purified preparations of Δ5 PLY and Δ6 PLY were observed to agglutinate erythrocytes in 96-well micro-titre plates but not lyse the cells; this effect was concentration dependent.

Example 4

Electron Microscopy

200 μl 2% (v/v) SRBC solution was incubated with an equal volume of 0.2 mg/ml WT PLY or Δ6 PLY at 37° C. for 20 minutes then centrifuged with benchtop centrifuge to pellet the SRBC membranes. Membranes were washed with $dH_2O$×3 and resuspended in 100 μl $dH_2O$. 5 μl of suspension was fixed onto carbon-coated grids and negatively stained with 1% phosphotungstate acid, pH6.8. Magnification was at ×25000 using an LEO 912 Energy Filter Transmission Electron Microscope.

Figure 5:
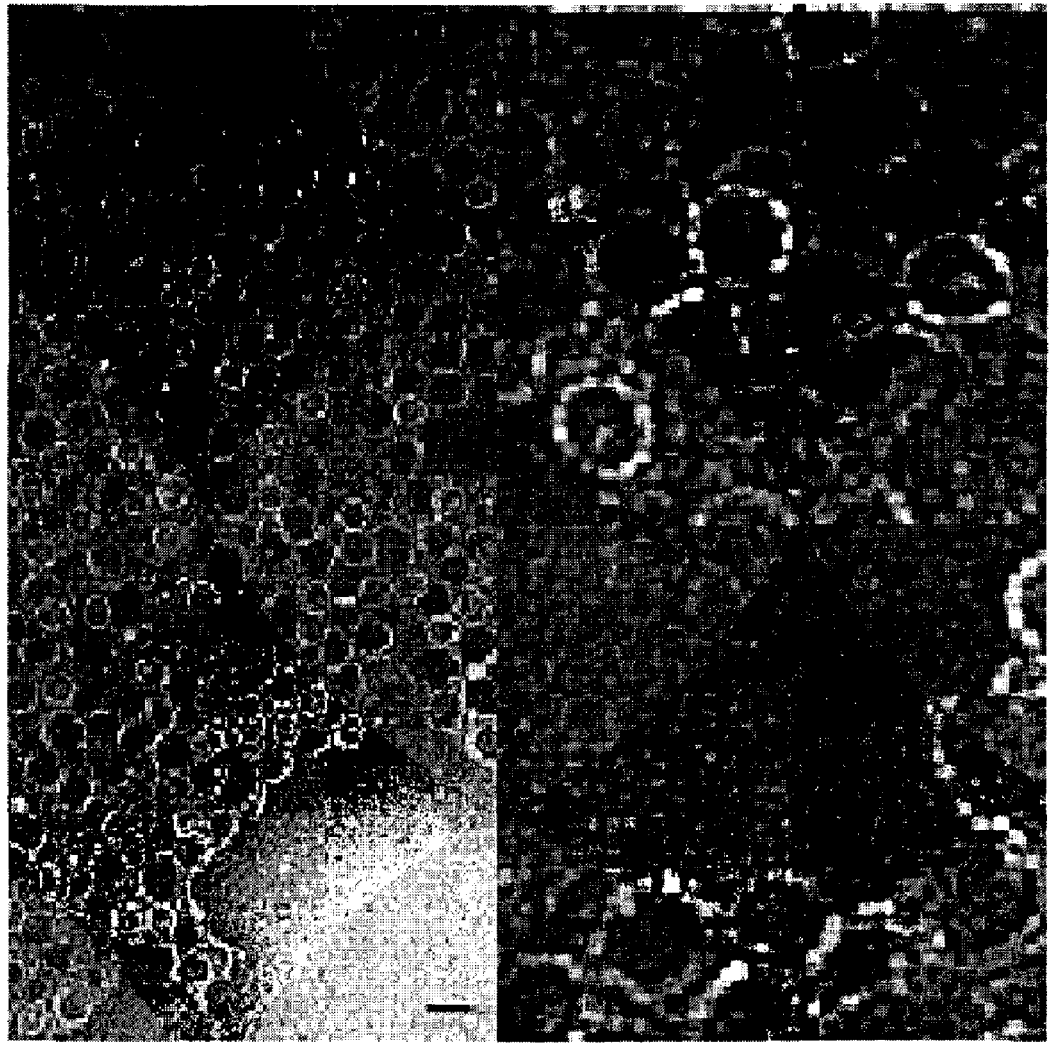
FIG. 5 shows electron micrographs of WT PLY treated erythrocyte membranes.

30-40 μm pores were visualised on erythrocyte membranes treated with 0.2 mg/ml WT PLY (FIG. 5). In contrast, pores were not visualised on membranes treated with 0-2 mg/ml Δ6 PLY.

Example 5

Western Blotting

PLY mutants created by site-directed mutagenesis were detected in Western blots using standard techniques. Blots were incubated with polyclonal anti-PLY serum from rabbit or monoclonal PLY 4 anti-PLY serum from mouse (de los Toyos et al, 1996) and then incubated with the relevant HRP-linked antibody (Amersham Life Sciences) and developed.

Of the eight double amino acid deletions created, all were recognised by Western blotting with polyclonal anti-PLY serum (not shown) and by mAb PLY 4 (FIG. 2) prepared by de los Toyos et al (1996).

Example 6

L929 Killing Assay

L929 murine fibroblasts (ECACC, no. 85011425) were cultured in RPMI 1640 media+10% Foetal Bovine Serum (FBS) (Gibco), passaged and transferred to a 96-well plate and incubated for 24 h at 37° C., 5% $CO_2$. Serial dilutions of purified WT PLY and mutant Δ6 PLY toxin were prepared in RPMI 1640 media from a stock concentration of 0.05 mg/ml and added to the L929 fibroblasts. Cell viability upon 24 h incubation with PLY was assessed using MTT (3-[4,5-Dimethylthiazol-2-yl]-2,5-diphenyltetrzolium bromide) (Sigma) which is degraded by mitochondrial activity into a purple formazan precipitate. MTT in wells with dead cells will remain yellow. Optical density was read at 540 nm with an MRX plate reader (Dynatech Laboratories).

Figure 4:
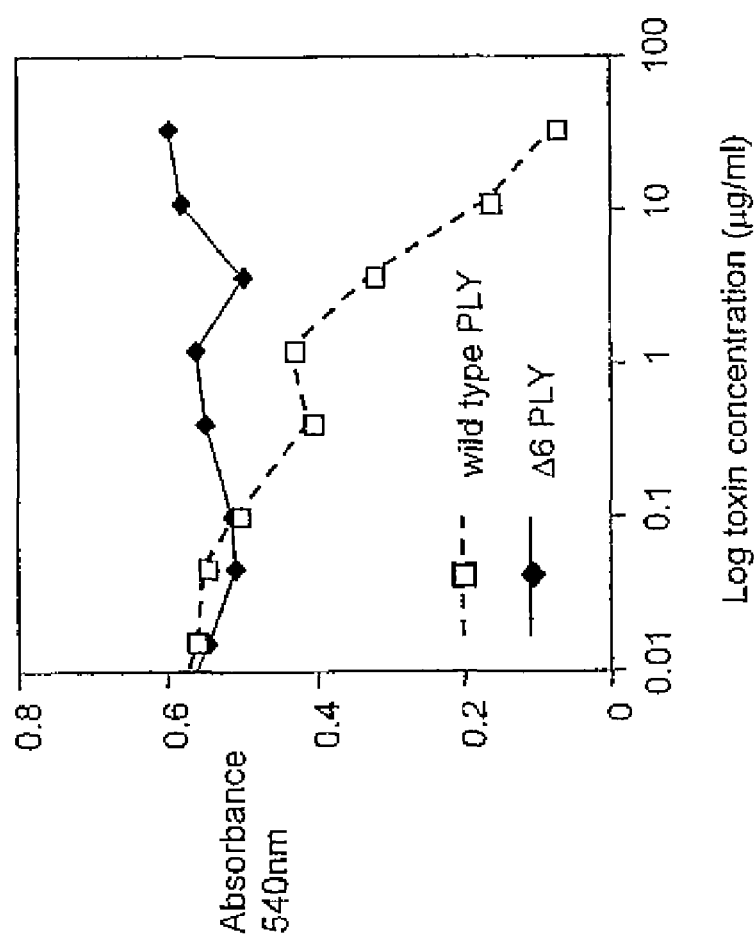
FIG. 4 shows the results of a cytotoxicity assay comparing WT PLY to Δ6 PLY mutant.

Cytotoxicity assays with L929 murine fibroblasts were run to assess the toxicity of mutant Δ6 PLY compared to WT PLY (FIG. 4). At concentrations of 30 μg/ml, Δ6 PLY was not toxic to fibroblasts, whereas <500 pg/ml of WT PLY was cytotoxic.

Example 7

In Vivo Cytokine Analysis

Eight week-old MF-1 mice (Harlan) were lightly anaesthetised with 2% halothane/1.5% oxygen (1.5 litre/min) (Zeneca). Purified LPS-free WT PLY was administered intranasally at 2 μg/dose and Δ6 PLY at 7 μg/dose (9.928 ng LPS/dose) in 50 μl volumes with a saline group as a control (n=4 for each treatment). Lipopolysaccharide (LPS) content of purified toxin was determined using the Limulus Amebocyte Lysate (LAL) Kinetic-QCL Kit (BioWhittaker) and run according to manufacturer's instructions. Mice were monitored to a 24 h end-point. Serum, bronchoalveolar lavage and lung tissue samples were recovered and processed as described previously (Kerr, et al. 2002). Cytokine levels were measured with commercial cytokine ELISA kits for Interleukin (IL)-6, Interferon (IFN)-γ (Pharmigen) and Tumor Necrosis Factor (TNF)-α (R&D systems, UK). Total protein levels in the lavage were measured using standard Bradford Assay.

Non-parametric analysis by Mann-Whitney U test was used to measure cytokine and total protein levels where $p<0.05$ was considered statistically significant. Values are expressed as medians±1 median absolute deviation (MAD) using Statview (Abacus Concepts).

As part of in vivo toxicity studies, gross symptoms were ascertained. All mice survived 24 hours post-treatment except one from the WT PLY group. Mice treated with Δ6 PLY and saline recovered from the anaesthetic quicker than mice given WT PLY. Behaviour of Δ6 PLY treated mice was similar to that of the saline control but WT PLY treated mice exhibited piloerection, laboured breathing and a hunched stance over a 6-hour period, recovering within the 24-hour time scale.

Figure 6:
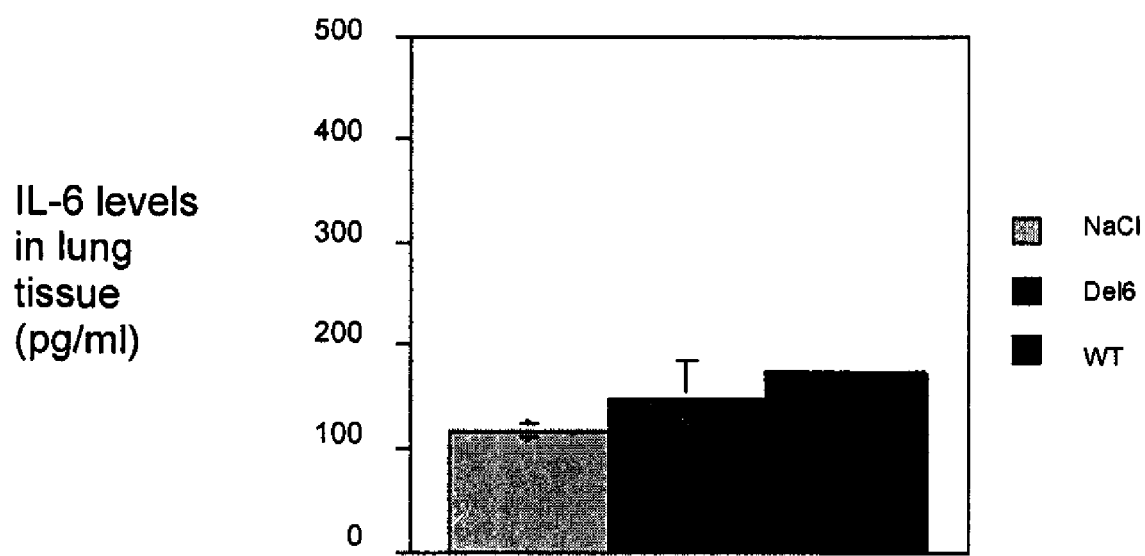
FIG. 6 shows IL-6 levels in lung tissue after treatment with WT PLY or Δ6 PLY.
Figure 7:
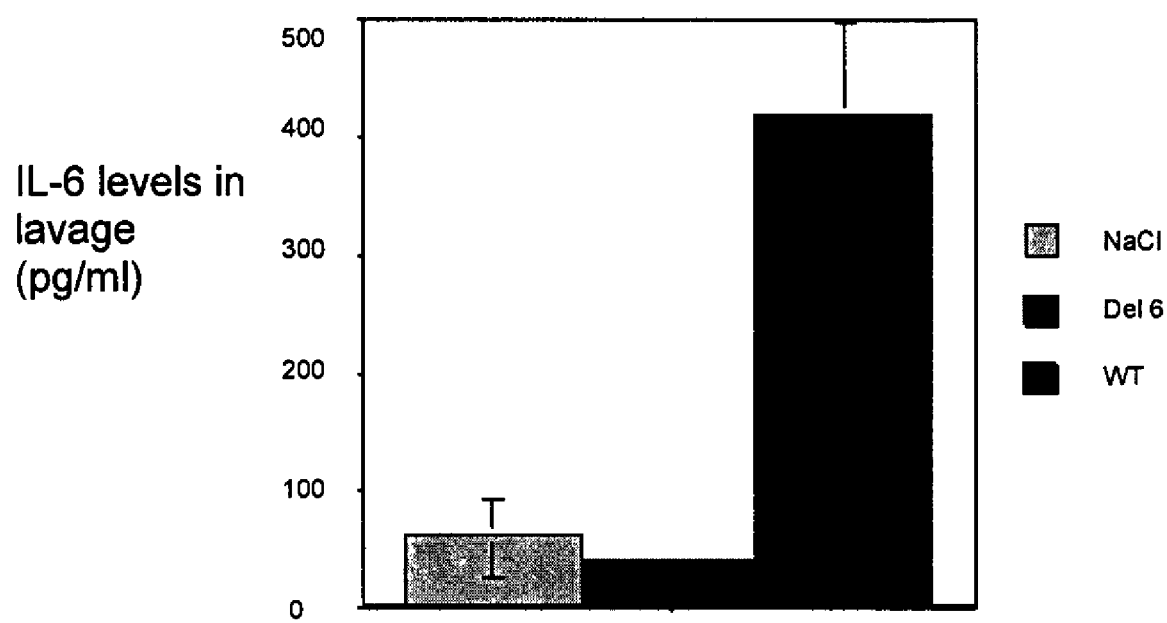
FIG. 7 shows IL-6 levels in lung lavage after treatment with WT PLY or Δ6 PLY.

Next, an inflammatory cytokine analysis was performed. IL-6 production was measured as a marker of toxicity of PLY to the host. There was a greater than 10-fold increase in IL-6 levels in the bronchoalveolar lavage of WT PLY treated mice (FIG. 7) compared to Δ6 PLY treatment ($p<0.05$) and the saline control ($p<0.05$). Treatment with WT PLY induces inflammation in the host airways whereas treatment with Δ6 PLY does not. The median IL-6 level in WT treated bronchoalveolar lavage was 416 pg/ml (range of 335-2225 pg/ml) whereas the background IL-6 level was low (59 pg/ml) with no increase in mice treated with Δ6 PLY (36 pg/ml) (see Table 3 below). An increase in IL-6 levels was observed in lung tissue of WT treated mice ($p<0.05$) compared to the saline control (FIG. 6). There was no significant IL-6 increase in lung tissue of Δ6 treated mice compared to the saline treatment. Measurements of IFN-γ and TNF-α were not significant between treatments 24 h post-administration (data not shown).

TABLE 3

IL-6 median (min-max) levels in bronchoalveolar lavage 24 h post treatment

| Treatment (i.n.) | Lung Tissue (pg/ml) | Lung Lavage (pg/ml) | P values (* = significant) | | 
|---|---|---|---|---|
| | | | | Lung | Lavage |
| NaCl | 117 (103-139) | 59 (19-113) | NaCl/Δ6 | 0.3865 | 0.7728 |
| Δ6 | 147 (73-209) | 36 (30-132) | Δ6/WT | 0.1573 | 0.0339* |
| Wild type (WT) | 171 (168-448) | 416 (335-2225) | NaCl/WT | 0.0339* | 0.0339* |

Figure 8:
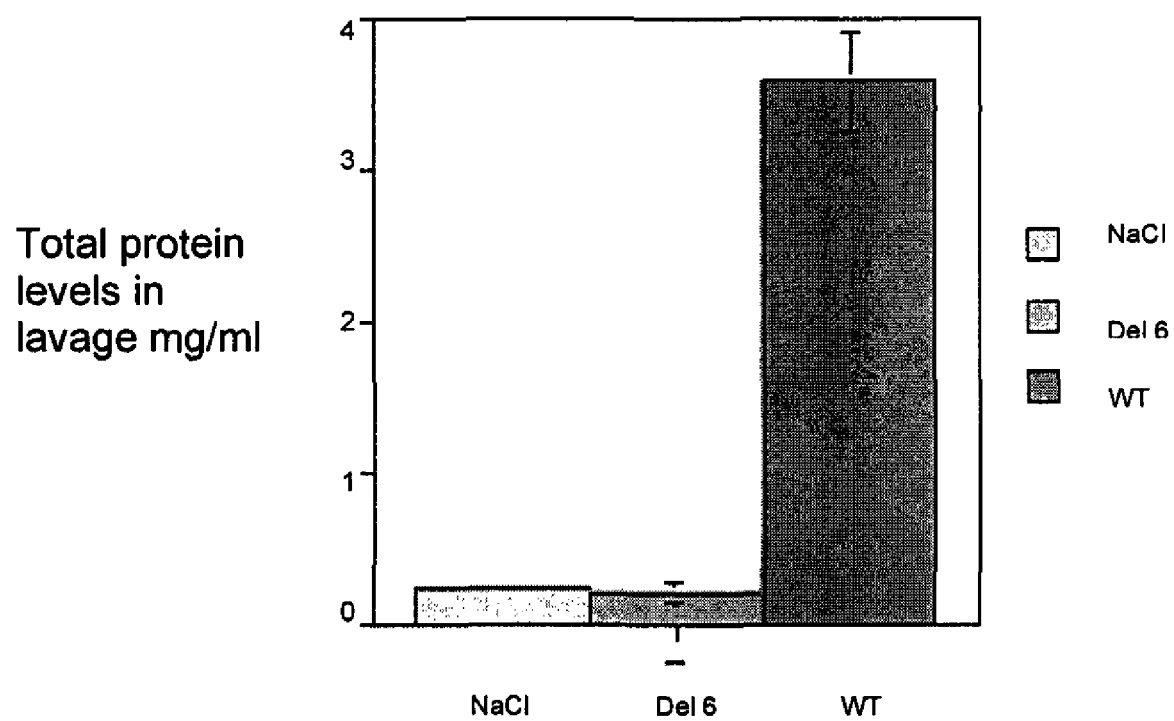
FIG. 8 shows total protein levels in bronchoalveolar lavage after treatment with WT PLY or Δ6 PLY.

Total protein levels (FIG. 8) were measured in the bronchoalveolar lavage to assess lung integrity. Increases in protein levels were not observed for Δ6 PLY treated mice compared to healthy lavage samples. Airways of WT PLY treated mice had large amounts of protein (3.57 mg/ml) in them compared to a background total protein level of 0.23 mg/ml for the saline control group (FIG. 8).

Example 8

Mouse Immunogenicity Studies

A mouse immunogenicity study was performed to compare responses of the wild type PLY protein to the Δ 5, 6 and 7 mutant proteins. All immunogenic compositions were prepared at 5 μg rPLY/dose in the presence of a combination of adjuvants, AlPO$_4$ (0.2 mg) and MPL-SE (50 μg). AlPO$_4$ (0.2 mg) and MPL-SE (50 μg) in phosphate-buffered saline (PBS) was used as a negative control.

Groups of 5 female, CD-1 mice, age 6-8 weeks, were immunized intraperitoneally and received 2 booster doses at 2 week intervals. Blood was collected retro-orbitally at weeks 0, 2, 4, and 6. Individual serum was assayed and GMTs represented an end point at 0.3. Week 0 antibodies were all <50. As shown in Table 4, the three PLY mutants elicited antibodies in the mice which were comparable to those elicited by wild type PLY.

TABLE 4

Serum IgG Antibody Responses to Mutant Recombinant Pneumolysin (rPLY) in Mice

| Immunogen | rPL Dose (μg) | GMT Antibodies for rPL Week | | |
|---|---|---|---|---|
| | | 2 | 4 | 6 |
| PBS | — | 50 | 50 | 50 |
| rPL (nlrPL 01-01) | 5.0 | 16,456 | 806,776 | 3,104,055 |
| rPL Wild type (PLY C73) | 5.0 | 11,420 | 578,645 | 997,727 |
| rPL Δ5 | 5.0 | 3,892 | 424,253 | 1,375,535 |
| rPL Δ6 | 5.0 | 18,679 | 999,574 | 1,452,972 |
| rPL Δ7 | 5.0 | 15,920 | 2,266,935 | 1,246,988 |

Example 9

Generation of Anti-PLY Antibodies

Figure 9:
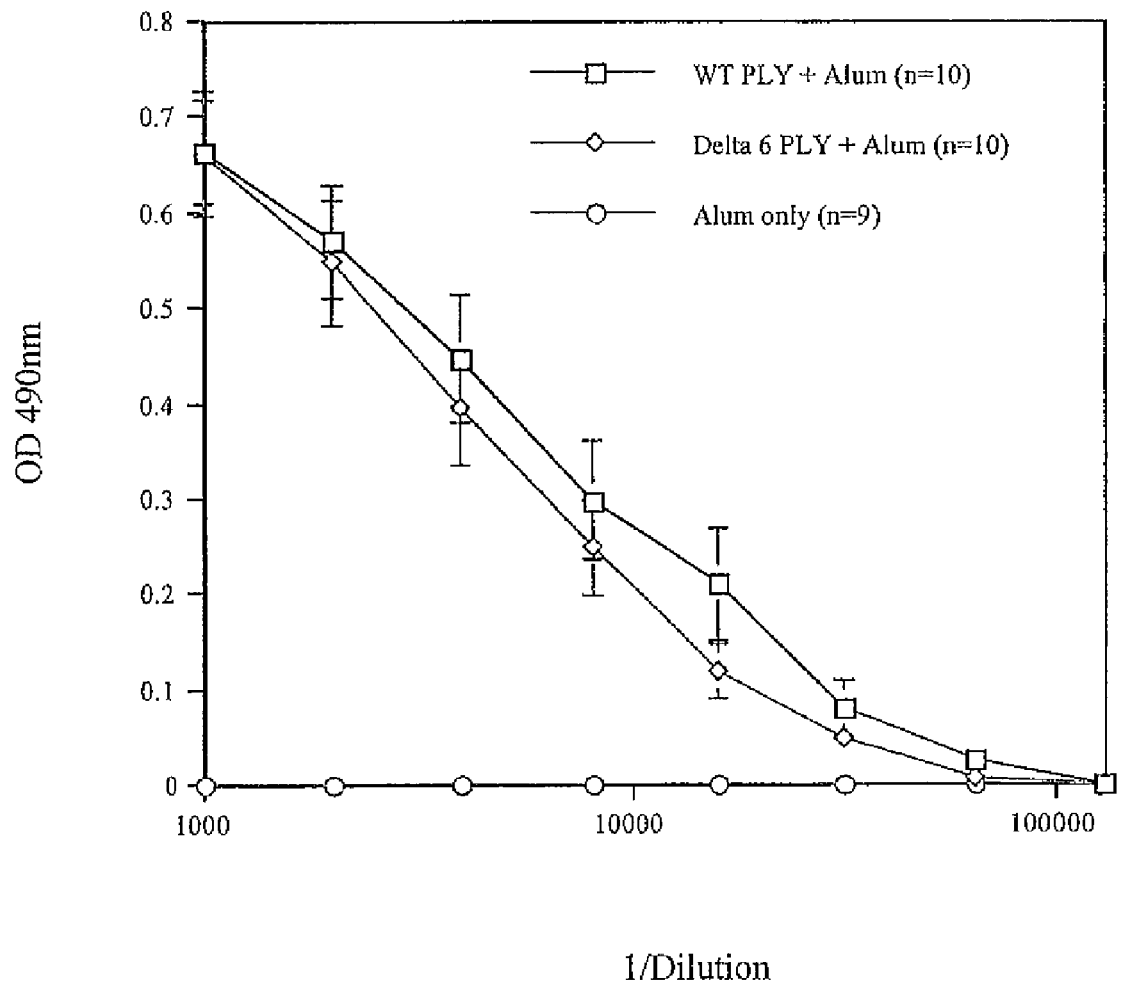
FIG. 9 shows anti-PLY antibody levels in response to immunization of mice with WT PLY or Δ6 PLY.

Levels of anti-PLY antibodies raised in mice immunized with wild type PLY or Δ6 PLY were determined by immunizing MF-1 mice with an initial subcutaneous injection with 20 μg WT PLY or Δ6 PLY, each with 100 μg Alum/100 μl dose. Mice were then boosted twice with the same dosage. Serum was collected on day 47 of the immunization protocol and analysed for anti-PLY IgG antibody. Antibody dilution curves are displayed in FIG. 9 as the group mean $OD_{490}$ nm±SEM against the serum serial dilution. An initial dilution of serum to 1/1000 was used as more concentrated samples resulted in complete saturation of the substrate. FIG. 9 demonstrates that high levels of antibodies were produced in response to both Δ6 PLY+Alum and WT PLY+Alum, but not to the Alum only control group.

Next, the ability of anti-PLY antibodies to neutralise the haemolytic activity was assessed. Anti-PLY antibodies in the Δ6 PLY and wild type PLY treated groups were observed to completely neutralise 2.5 Haemolytic Units (HU) of PLY to a titre of 1000-2400 in a haemolytic assay (where neutralising ability is expressed as the reciprocal of the antibody dilution that completely neutralises 2.5 HU of PLY) (data not shown). This demonstrates that a neutralising site on PLY is recognised and bound to by the antibodies produced in response to immunisation with Δ6 PLY+Alum and WT PLY+Alum. Because Δ6 PLY is non-toxic and does not induce the in vivo levels of cytokine production observed with wild type PLY treatment, Δ6 PLY is therefore a more favourable protein than wild type PLY for use as an immunogenic carrier protein.

Example 10

Effect of a Single Amino Acid Deletion

Figure 10:
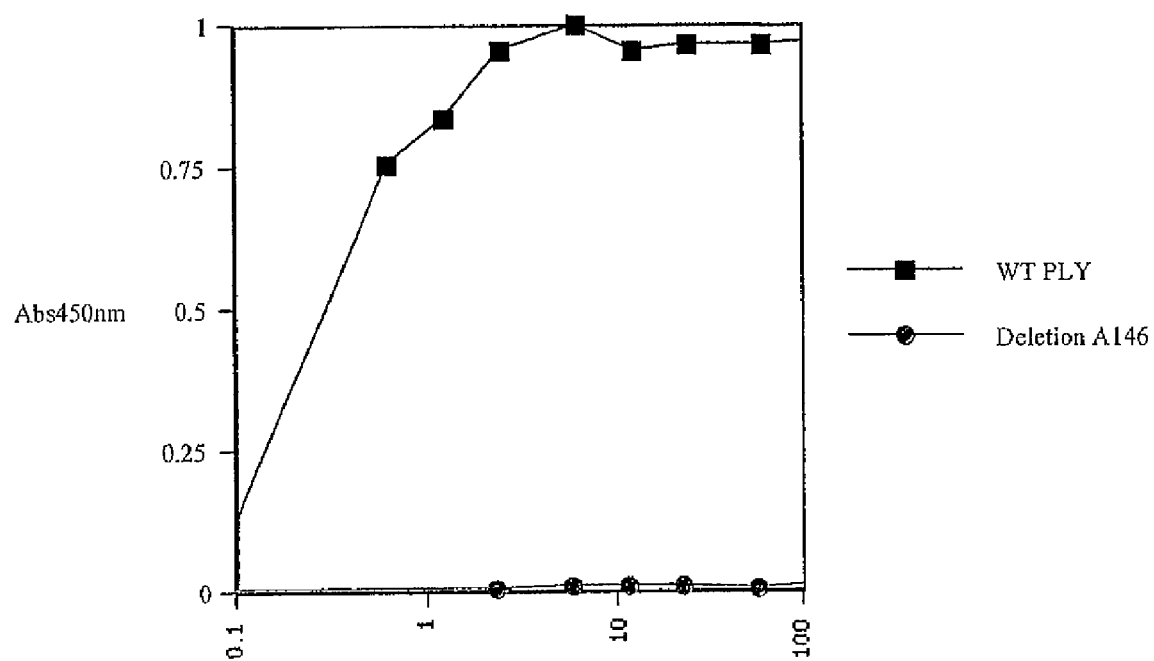
FIG. 10 shows the degree of haemolysis in relation to toxin concentration in SRBC (sheep red blood cell) treated with WT PLY or the deletion mutant ΔA146 PLY.

A mutant PLY was generated which had a single amino acid deletion: the alanine at amino acid 146 was deleted (ΔA146 PLY). As shown in FIG. 10, this single deletion (ΔA146) also resulted in a non-haemolytic form of PLY. ΔA146 PLY was not haemolytic to SRBC to concentrations >100 μg/ml, whereas wild type PLY was haemolytic at concentrations <1 μg/ml. Production of this mutant was confirmed by sequencing and by Western blotting of the expressed protein with polyclonal anti-PLY serum (data not shown).

Example 11

Haemolytic Activity of PLY Mutants in Comparison to PLY W433F

The haemolytic activity of the deletion mutants Δ6, Δ7, Δ8 PLY and ΔA146 PLY against human erythrocytes was compared with that of WT PLY and PLY mutant carrying the substitution W433F, which has previously been described to possess only 1% of the haemolytic activity of WT PLY (see WO90/06951).

Figure 11:
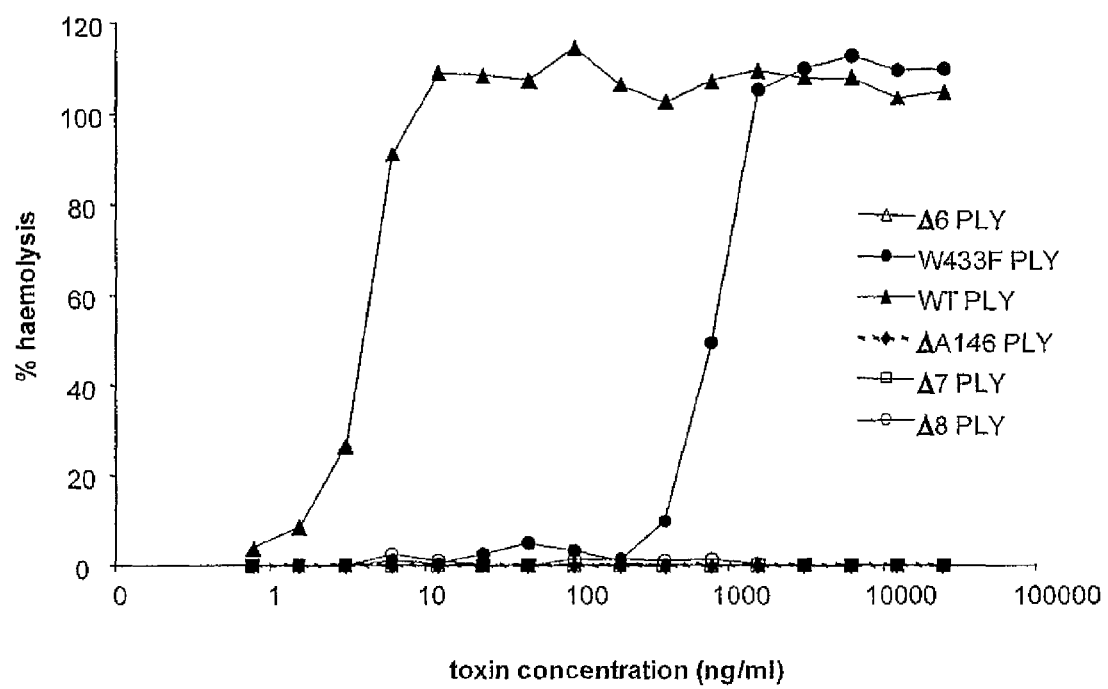
FIG. 11 compares the haemolytic activity of WT PLY and the mutants PLY W433F, Δ6 PLY, Δ7 PLY, Δ8 PLY and ΔA146 PLY.

FIG. 11 shows that, as expected, the W433F mutant shows ~1% of the haemolytic activity of wild type PLY. However the deletion mutants do not cause lysis of human erythrocytes at all.

Example 12

Binding of GFP-Tagged PLY to Erythrocyte Membranes

Fluorescence microscopy was used to visualise erythrocytes treated with eGFP-tagged forms of WT PLY and Δ6 PLY.

Erythrocyte ghosts were prepared from human blood by repeated washing with distilled water. Erythrocyte ghosts generated from 0.1 ml human blood were incubated with 50 μg EGFP-PLY or 50 μg Δ6EGFP-PLY in 1 ml 1×PBS for 30 min at 37° C. The ghost membranes were pelleted, washed ×3 in PBS and were visualized by fluorescence microscopy using a Zeiss Axioscop 20.

The results (not shown) demonstrate that the binding of Δ6 PLY to membranes is substantially the same as that of WT PLY.

Example 13

Analysis of Pore Formation Using Transmission Electron Microscopy

Electron microscopy was performed as described above (Example 4) for negatively stained horse erythrocyte membranes treated with 0.2 mg/ml wild type pneumolysin, 0.2 mg/ml W433F PLY, and 0.2 mg/ml ΔA146 PLY.

Pores were observed on membranes treated with wt PLY and W433F but not on membranes treated with ΔA146 PLY. Instead, ΔA146 PLY treatment resulted in the formation of long chains, thought to contain self-associated toxin that is unable to oligomerise to form pores. (Data not shown.)

Thus Δ6 PLY retains the membrane-binding properties of wild type PLY but does not form pores in cell membranes.

Example 14

Cytotoxicity of Pneumolysin Mutants to Murine L929 Fibroblasts

Figure 12:
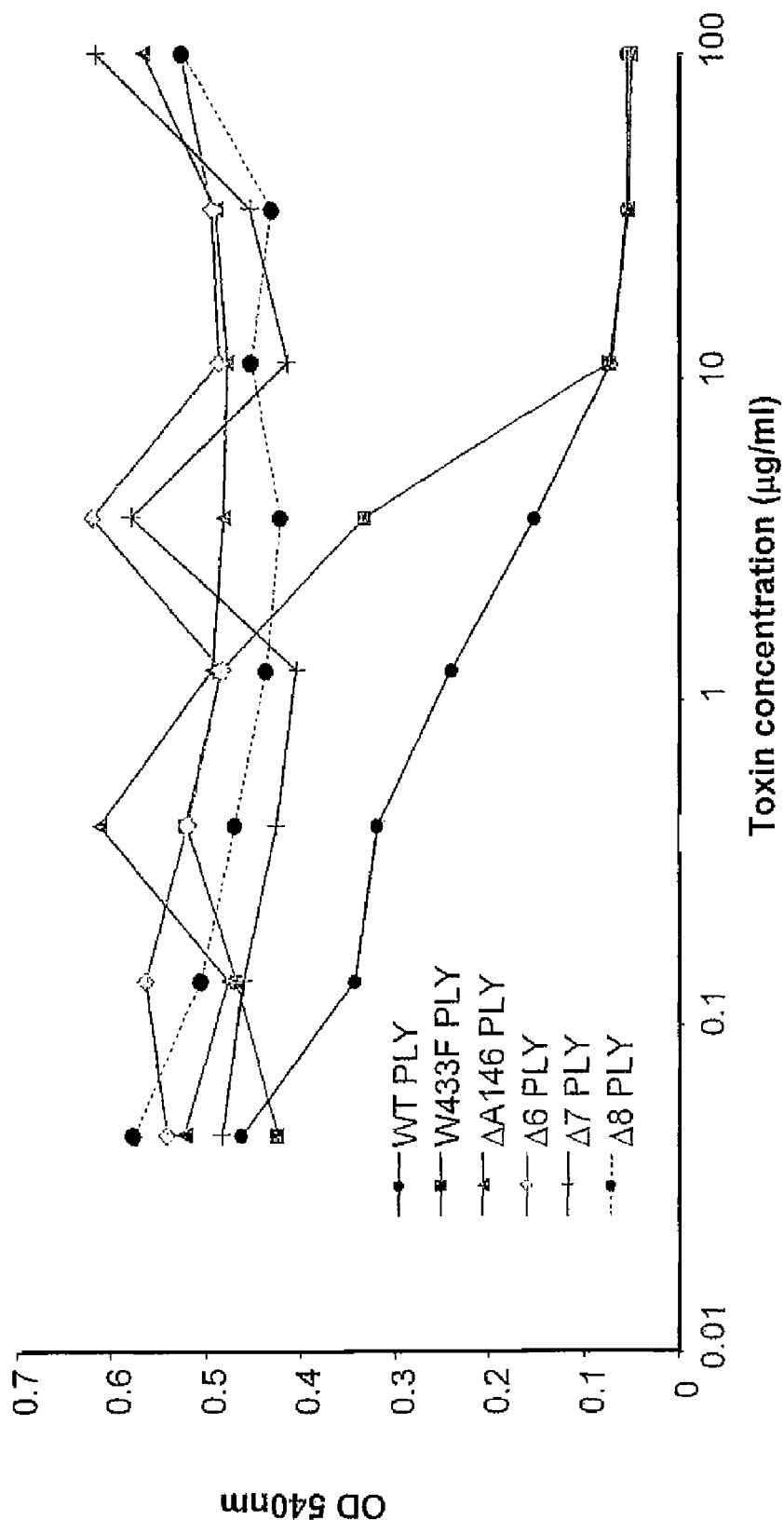
FIG. 12 shows the cytotoxicity to murine L929 fibroblasts of WT PLY and the mutants PLY W433F, Δ6 PLY, Δ7 PLY, Δ8 PLY and ΔA146 PLY.

The cytotoxicity of WT PLY, PLY W433F, and deletion mutants Δ6, Δ7, Δ8 PLY and ΔA146 PLY against murine L929 fibroblasts was determined as described in Example 6. human erythrocytes was compared with that of WT PLY and The W433F PLY mutant was found to be cytotoxic at 10 μg/ml and above, whereas the deletion mutants were non-toxic in this assay (FIG. 12).

Example 15

Cytotoxicity of Pneumolysin Mutant ΔA146 PLY to RBL-2H3 Mast Cells

The cytotoxicity of ΔA146 PLY against rat RBL-2H3 mast cells was assessed using a degranulation assay.

The assay was carried out as described by Stassen et al (2003) using $10^4$ cells/well, incubated with wild type PLY or ΔA146 PLY for 90 minutes.

Figure 13:
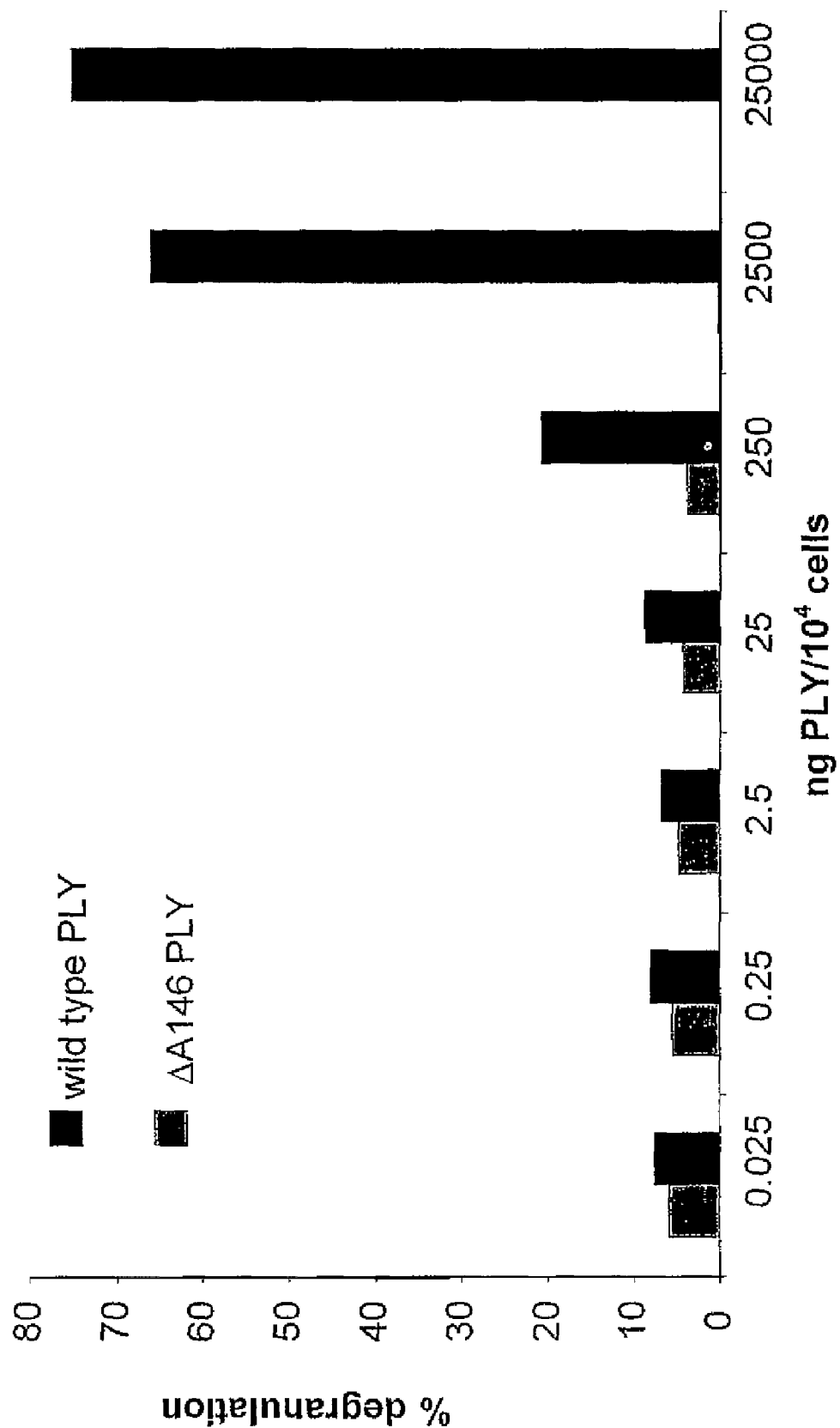
FIG. 13 shows that ΔA146 PLY does not cause degranulation of RBL-2H3 mast cells, while WT PLY does.

Release of β-hexosaminidase from mast cell granules was measured, which gives a direct measure of the degranulation of the cells in response to the toxin. ΔA146 PLY did not cause mast cell degranulation (FIG. 13).

Example 16

Analysis of Murine Core Body Temperature Following Treatment with wt PLY or ΔA146 PLY Balb/c mice were implanted with telemetry chips which enable acquisition of core body temperature (Tc). Mice were treated with 1 μg wt PLY, 1 μg ΔR146PLY, or saline solution alone.

Figure 14:
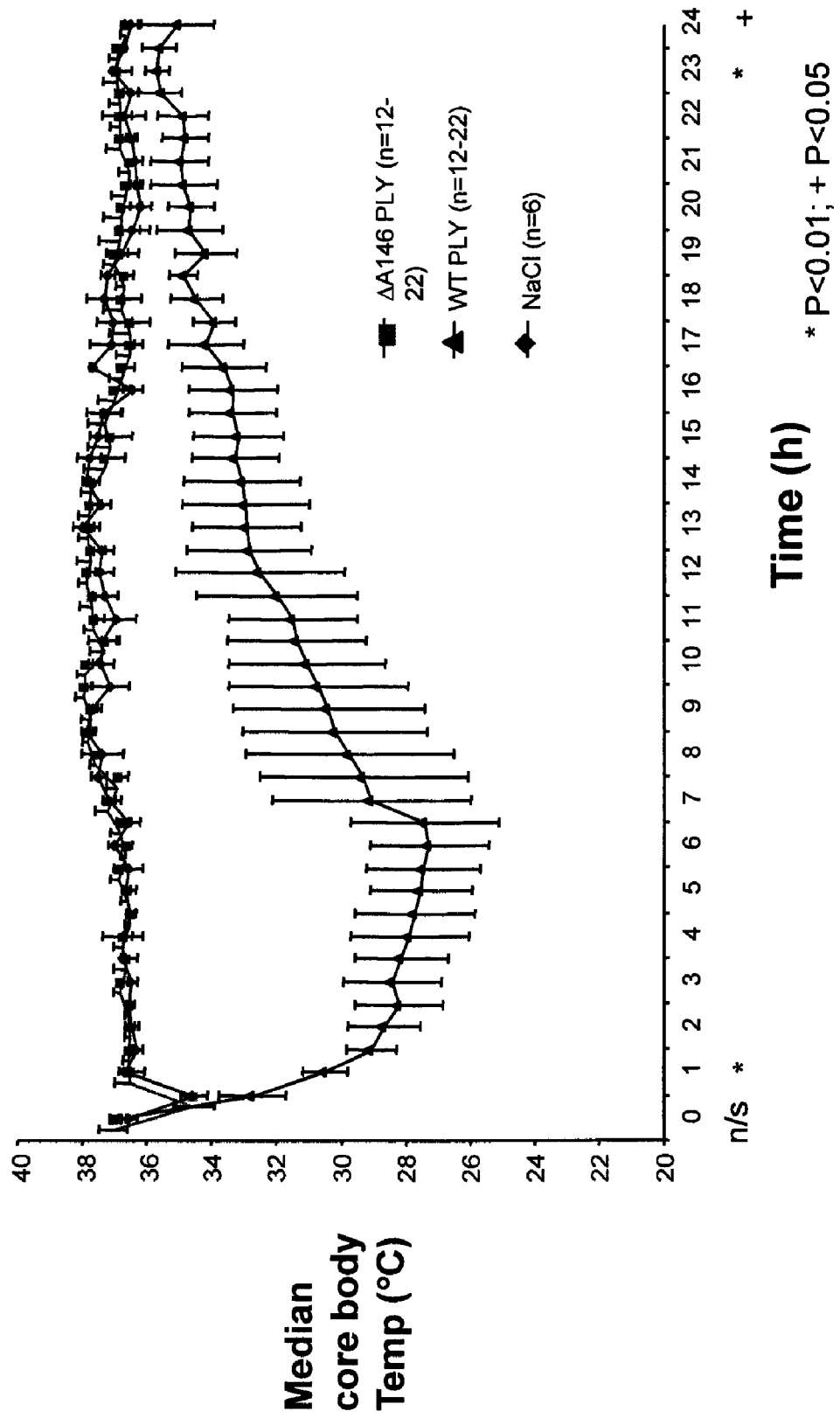
FIG. 14 shows analysis of core body temperature following treatment with wild type PLY or ΔA146 PLY.

As shown in FIG. 14, Treatment with WT PLY resulted in a severe hypothermic response with Tc dropping to 28° C. This Tc was sustained for 6 hours after which there was an increase in Tc by ~0.6° C./hour and by 24 hours this was similar to the Tc of the control group, though still statistically significant. Treatment with ΔA146 PLY did not result in hypothermia and the median Tc was comparable to the saline control group.

Thus, treatment of mice with WT PLY resulted in a sustained hypothermic response that was not observed following treatment with the same amount of ΔA146 PLY.

While the invention has been described in conjunction with the exemplary embodiments described above, many equivalent modifications and variations will be apparent to those skilled in the art when given this disclosure. Accordingly, the exemplary embodiments of the invention set forth are considered to be illustrative and not limiting. Various changes to the described embodiments may be made without departing from the spirit and scope of the invention. All references cited herein are expressly incorporated by reference.

REFERENCES

Alexander, J. E., Lock, R. A., Peeters, C. C. A. M., Poolman, J. T., Andrew, P. W., Mitchell, T. J., Hansman, D. and Paton, J. C. (1994) Immunization of mice with pneumolysin toxoid confers a significant degree of protection against at least nine serotypes of Streptococcus pneumoniae. Infect. Immun. 62:5686-5688

Aslam and Dent (1998), "Bioconjugation: Protein Coupling Techniques for the Biomedical Sciences," Macmillan Reference Ltd., London, England Berry, A. M., Alexander, J. E., Mitchell, T. M., Andrew, P. W., Hansman, D, and Paton, J. C. (1995) Effect of defined point mutations in the pneumolysin gene on the virulence of Streptococcus pneumoniae. Infect. Immun. 63:1969-1974

Bhakdi, S., Tranum-Jensen, J. and Sziegoleit, A. (1985) Mechanism of membrane damage by Streptolysin O. Infect. Immun. 47:52-60

Blum, M. D., Dagan, R, Mendelman, P. M., Pinsk, V., Giordani, M., Li, Shu, Bohidar, N. and McNeely, T. B. (2000) A comparison of multiple regimens of pneumococcal polysaccharide-meningococcal outer membrane protein complex conjugate vaccine and pneumccoccal polysaccharide vaccine in toddlers. Vaccine 18:2359-2367

Bonev B., Gilbert, R. and Watts, A. (2000) Structural investigations of pneumolysin/lipid complexes. Molecular Membrane Biology 17:229-235

Cockeran, R., Anderson, R. and Feldman, C. (2002) The role of pneumolysin in the pathogenesis of Streptococcus pneumoniae infection. Current Opinion in Infectious Diseases 15:235-239

Hausdorff, W. P., Bryant, J., Paradiso, P. R. and Siber, G. R. (2000) Which pneumococcal serogroups cause the most invasive disease: implications for conjugate vaccine formulation & use, part I. Clinical Infect. Dis. 30:100-121

Hotze, E. M., Heuck, A. P., Czajkowsky, D. M., Shao, Z., Johnson A. E., and Tweten, R. K. (2002) Monomer-monomer interactions drive the prepore to pore conversion of a β-barrel-forming cholesterol-dependent cytolysin. J. Biol. Chem. 277:11597-11605

Hugo, F., Reichwein, J., Arvand, M., Krämer, S., and Bhakdi, S. (1986) Use of monoclonal antibody to determine the mode of transmembrane pore formation by streptolysin O. Infect. Immun. 54:641-645

Kadioglu, A., Gingles, N. A., Grattan, K., Kerr, A., Mitchell, T. J. and Andrew, P. W. (2000) Host cellular immune response to Pneumococcal lung infection in mice. Infect. Immun. 68:492-501

Kalin, M (1998) Pneumococcal serotypes & their clinical relevance. Thorax 53:159-162

Katcocin, D. M. (2000) Characterisation of multivalent pneumococcal conjugate vaccines. Dev. Biol. (Basel) 103:113-119

Kerr, A. R., Irvine, J. J., Search, J. J., Gingles, N. A., Kadioglu, A., Andrew P. W., McPheat, W. L., Booth, C. G., and Mitchell T. J. (2002) Role of inflammatory mediators in resistance and susceptibility to pneumococcal infection. Infect. Immun. 70:1547-1557

Klein, D. (1995) Pneumococcal conjugate vaccines: review and update. Microbial Drug Resist. 1:49-58

Kyaw, M. H., Clarke, S., Jones, I. G. and Campbell, H. (2002) Non-invasive pneumococcal disease and antimicrobial resistance: vaccine implications. Epidemiol. Infect. 128: 21-27

Kyaw, M. H., Clarke, S., Edwards, G. F. S., Jones, I. G., and Campbell, H. (2000) Serotypes/groups distribution and antimicrobial resistance of invasive pneumococcal isolates. Epidemiol. Infect. 125(3) 561-572

Mitchell, T. J., Andrew, Boulnois, G. J., Lee, C. J., Lock, R. A. and Paton, J. C. (1992) Molecular studies of pneumolysin, the thiol-activated toxin of Streptococcus pneumoniae as an aid to vaccine design. Bacterial protein toxins 23:429-438

Mitchell, T. J., Walker, J. A., Saunders, F. K., Andrew P. W. and Boulnois, G. J. (1989) Expression of the pneumolysin gene in Escherichia coli: rapid purification and biological properties. Biochimica et Biophysica Acta 1007:67-72

Morgan, P. J., Varley, P. G., Rowe, A. J., Andrew, P. W. and Mitchell, T. J. (1993) Characterisation of the solution properties and conformation of pneumolysin, the membrane damaging toxin of Streptococcus pneumoniae. Biochem. J. 296:671-674

Morgan, P. J., Harrison, G., Freestone, P. P. E., Crane, D., Rowe, A. J., Mitchell, T. J., Andrew, P. W. and Gilbert, R. J. C. (1997) Structural and functional characterisation of two proteolytic fragments of the bacterial toxin, pneumolysin. FEBS letters 412:563-567

Obaro, S. K. (2001) Confronting the pneumococcus: a target shift or bullet change? Vaccine 19:1211-1217

Palmer, M. (2001) The family of thiol-activated, cholesterol-binding cytolysins. Toxicon 39:1681-1689

Paton, J. C. (1996) The contribution of pneumolysin to the pathogenicity of Streptococcus pneumoniae. Trends in Microbiology 4(3):103-106

Paton, J. C., Andrew, P. W., Boulnois, G. J. and Mitchell, T. J. (1993) Molecular analysis of the pathogenicity of Streptococcus pneumoniae: the role of pneumococcal proteins. Annu. Rev. Microbiol. 47:89-115

Paton, J. C., Lock, R. A., Lee, C. J., Li, J. P., Berry, A. M., Mitchell, T. J., Andrew, P. W., Hansman, D. and Boulnois, G. J. (1991) Purification and immunogenicity of genetically obtained pneumolysin toxoids and their conjugation to Streptococcus pneumoniae type 19F polysaccharide. Infect. Immun. 59: 2297-2304

Rayner, C. F. J., Jackson, A. D., Rutman, A., Dewar, A., Mitchell, T. J., Andrew, P. W., Cole, P. J. and Wilson, R. (1995) Interaction of pneumolysin-sufficient and deficient isogenic variants of Streptococcus pneumoniae with human respiratory mucosa. Infect. Immun. 63:442-447

Rijneveld, A. W., van den Dobbelsteen, G. P., Florquin, S., Standiford, T. J., Speelman, P., van Alphen, L. and van der Poll, T. (2002) Roles of interleukin-6 and macrophage inflammatory protein-2 in pneumolysin-induced lung inflammation in mice. Journal of Infectious. Diseases. 185: 123-126

Rubins, J. B. and Janoff, E. N. (1998) Pneumolysin: A multifunctional pneumococcal virulence factor. *J. La. Clin. Med.* 131:21-27

Salo, S., Närvänen, A., and Leinonen, M. (1993) Mapping of immunoreactive sites of pneumococcal pneumolysin by use of synthetic peptides. *Infect. Immun.* 61:2822-2826

Saunders, F. K., Mitchell, T. J., Walker, J. A., Andrew, P. W. and Boulnois, G. J. (1989) Pneumolysin, the thiol-activated toxin of *Streptococcus pneumoniae*, does not require a thiol group for in vitro activity. *Infect. Immun.* 57:2547-2552

Search, J. J. (2002) The role of pneumolysin in proinflammatory mediator production. PhD Thesis, University of Glasgow Shepard, L. A., Heuck, A. P., Hamman, B. D., Rossjohn, J., Parker M. W., Ryan, K. R., Johnson, R. E. and Tweten, R. W. (1998) Identification of a membrane-spanning domain of the thiol-activated pore-forming toxin *Clostridium perfringens* Perfringolysin O: An α-helical to β-Sheet transition identified by fluorescence spectroscopy. *Biochemistry* 37:14563-14574

Stassen, M., Müller, C., Richter, C., Neudörfl, C., Hültner, L., Bhakdi, S., Walev, I. and Schmitt, E. (2003) The Streptococcal Exotoxin Streptolysin O Activates Mast Cells To Produce Tumor Necrosis Factor Alpha by p38 Mitogen-Activated Protein Kinase- and Protein Kinase C-Dependent Pathways. *Infect Immun,* 71(11): 6171-6177.

Suárez-Álvarez, B., del Mar Garcia Suárez, M., Méndez, F. J. and de los Toyos, J. R. (2003). Characterisation of mouse monoclonal antibodies for pneumolysin: fine epitope mapping and V gene usage. *Immun. Letters* 00:1-13 de los Toyos, J. R., Méndez, F. J., Aparicio, J. F., Vázquez, F., del Mar Garcia Suárez, M., Fleites, A., Hardisson, C., Morgan P. J., Andrew P. W., and Mitchell T. J. (1996). Functional analysis of pneumolysin by use of monoclonal antibodies. *Infect. Immun.* 64:480-484

Walker J. A., Allen, R. L., Falmange, P., Johnson, M. K. and Boulnois, G. J. (1987) Molecular cloning, characterisation, and complete nucleotide sequence of the gene for pneumolysin, the sulfhydryl-activated toxin of *Streptococcus pneumoniae*. *Infect. Immun.* 55:1184-1189

Whitney C. G., Farley M. M., Hadler J., Harrison L. H., Bennett N. M., Lynfield R., Reingold A., Cieslak P. R., Pilishvili T., Jackson D., Facklam R. R., Jorgensen J. H., Schuchat A. (2003) Decline in invasive pneumococcal disease after the introduction of protein-polysaccharide conjugate vaccine. *N. Eng. J. Med.* 348:1737-1746

The invention claimed is:

1. An isolated mutant pneumolysin (PLY) protein comprising at least 95% sequence identity to a wild type PLY protein set forth in SEQ ID NO: 1, wherein one or more amino acids within the region of amino acids 144 to 151 of SEQ ID NO: 1 is deleted and wherein the isolated mutant PLY protein has reduced toxicity compared to the wild-type PLY protein.

2. The protein of claim 1, wherein alanine 146 of SEQ ID NO: 1 is deleted.

3. The protein of claim 1, wherein at least one amino acid substitution or deletion is in one or more regions of amino acids selected from the group consisting of:

(a) 257-297,
(b) 367-397; and
(c) 424-437 of SEQ ID NO: 1.

4. A composition comprising the protein of claim 1, in a physiologically acceptable adjuvant, diluent or carrier.

5. The protein of claim 1, wherein two adjacent amino acids within the region of amino acids 144 to 151 of SEQ ID NO:1 are deleted.

6. The protein of claim 5, wherein amino acids valine 144 and proline 145 of SEQ ID NO: 1 are deleted.

7. The protein of claim 5, wherein amino acids alanine 146 and arginine 147 of SEQ ID NO: 1 are deleted.

8. The protein of claim 5, wherein amino acids methionine 148 and glutamine 149 of SEQ ID NO: 1 are deleted.

9. The protein of claim 5, wherein amino acids tyrosine 150 and glutamic acid 151 of SEQ ID NO: 1 are deleted.

10. An immunogenic composition comprising:
   (a) a saccharide, oligosaccharide, polysaccharide, peptide, polypeptide or protein; and
   (b) the isolated mutant PLY protein of claim 1 in a physiologically acceptable adjuvant, diluent or carrier.

11. The immunogenic composition of claim 10, wherein the saccharide, oligosaccharide or polysaccharide is derived from *Streptococcus pneumoniae*.

12. The immunogenic composition of claim 11, wherein there are a plurality of *Streptococcus pneumoniae* serotypes.

13. The immunogenic composition of claim 10, wherein at least one amino acid substitution or deletion is in one or more regions of amino acids selected from the group consisting of:
   (a) 257-297,
   (b) 367-397; and
   (c) 424-437 of SEQ ID NO: 1.

14. The immunogenic composition of claim 10, wherein two adjacent amino acids within the region of amino acids 144 to 151 of SEQ ID NO: 1 are deleted.

15. The immunogenic composition of claim 14, wherein amino acids valine 144 and proline 145 of SEQ ID NO:1 are deleted.

16. The immunogenic composition of claim 14, wherein amino acids alanine 146 and arginine 147 of SEQ ID NO:1 are deleted.

17. The immunogenic composition of claim 14, wherein amino acids methionine 148 and glutamine 149 of SEQ ID NO:1 are deleted.

18. The immunogenic composition of claim 14, wherein amino acids tyrosine 150 and glutamic acid 151 of SEQ ID NO:1 are deleted.

19. An immunogenic conjugate comprising:
   (a) a saccharide, oligosaccharide, polysaccharide, peptide, polypeptide or protein; and
   (b) the isolated mutant pneumolysin (PLY) protein of claim 1.

20. The immunogenic conjugate of claim 19, wherein the saccharide, oligosaccharide or polysaccharide is derived from *Streptococcus pneumoniae*.

21. The immunogenic conjugate of claim 19, wherein at least one amino acid substitution or deletion is in one or more regions of amino acids selected from the group consisting of:
   (a) 257-297,
   (b) 367-397; and
   (c) 424-437 of SEQ ID NO: 1.

22. The immunogenic conjugate of claim 19, wherein alanine 146 of SEQ ID NO: 1 is deleted.

23. The immunogenic conjugate of claim 19, wherein two adjacent amino acids within the region of amino acids 144 to 151 of SEQ ID NO: 1 are deleted.

24. The immunogenic conjugate of claim 23, wherein amino acids valine 144 and proline 145 of SEQ ID NO: 1 are deleted.

25. The immunogenic conjugate of claim 23, wherein amino acids alanine 146 and arginine 147 of SEQ ID NO: 1 are deleted.

26. The immunogenic conjugate of claim 23, wherein amino acids methionine 148 and glutamine 149 of SEQ ID NO: 1 are deleted.

27. The immunogenic conjugate of claim 23, wherein amino acids tyrosine 150 and glutamic acid 151 of SEQ ID NO: 1 are deleted.

* * * * *